US006696560B1

United States Patent
Durfee et al.

(10) Patent No.: US 6,696,560 B1
(45) Date of Patent: Feb. 24, 2004

(54) **RETINOBLASTOMA-LIKE RRB GENE OF *ARABIDOPSIS THALIANA***

(75) Inventors: Tim Durfee, Madison, WI (US); Heidi Feiler, Berkeley, CA (US); Wilhelm Gruissem, Berkeley, CA (US); Susan Jenkins, Briones Valley, CA (US); Judith Roe, Manhattan, KS (US); Patricia Zambryski, Berkeley, CA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/527,084

(22) Filed: Mar. 16, 2000

Related U.S. Application Data

(60) Provisional application No. 60/125,229, filed on Mar. 19, 1999.

(51) Int. Cl.$^7$ .............................................. C12N 15/29
(52) U.S. Cl. .................................. 536/23.6; 435/320.1
(58) Field of Search ............................ 435/69.1, 320.1, 435/410, 419, 468; 536/23.6; 800/278, 287, 290, 295, 298

(56) References Cited

FOREIGN PATENT DOCUMENTS

| WO | WO9747647 | 12/1997 | ......... C07K/14/415 |
| WO | WO9747745 | 12/1997 | ........... C12N/15/29 |

OTHER PUBLICATIONS

James G. Umen et al., Control of cell division by a retinoblastoma protein homolog in Chlamydomonas, Gene & Development, vol. 15, pp. 1652–1661, 2001.*
Ach et al, "A Conserved Family of WD–40 Proteins Binds to the Retinoblastoma Protein in Both Plants and Animals", Plant Cell, 1997, 9(9): p. 1595–1606.
Ach et al, "RRB1 and RRB2 Encode Maize Retinoblastoma–Related Proteins That Interact with a Plant D–type Cyclin and Geminivirus Replication Protein", Molecular and Cellular Biology, 1997, 17(9): p. 5077–5086.
de Jager et al, "Retinoblastoma proteins in plants", Plant Molecular Biology, Oct., 1999, 41(3): p. 295–299.
Grafi, G., et al., "A maize cDNA encoding a member of the retinoblastoma protein family: Involvement in endoreduplication." Proceedings of the National Academy of Science of the United states of America, 1996. 93(17); p. 8962–8967.
Gutierrez, C., "The retinoblastoma pathway in plant cell cycle and development". Current Opinion in Plant Biology, 1998. 1(6): p. 492–497.
Gutierrez, C., "DNA replication and cell cycle in plants: learning from geminiviruses." EMBO (European Molecular Biology Organization) Journal., 2000. 19(5): p. 792–799.
Huntley, R., et al., "The maize retinoblastoma protein homologue ZMRb–1 is regulated during leaf development and displays conserved interactions with G1/S regulators and plant cyclin D (CycD) proteins." Plant Molecular Biology, 1998. 37(1): p. 155–169.
Kan, H.G. et al, "A glucocorticoid–inducible transcription system causes serve growth defects in Arabiodopsis and induces defense–related genes", Plant Journal, Oct. 1999. 20(1): p. 127–133.
Liu, L., et al., "Bean Yellow Dwarf Virus RepA, but Not Rep, Binds to Maize Retinoblastoma Protein, and the Virus Tolerates Mutations in the Consensus Binding Motif", Virology, Apr., 1999. 256(2): p. 270–279.
Loidl, A. et al., "Oncogene– and tumor–suppressor gene–related proteins in plants and fungi." Critical Reviews in Oncogenesis, 1996. 7(1–2): p. 49–64.
Nakagami, H., et al., "Tobacco retinoblastoma–related protein Phophorylated by a Distinct cyclin–dependent kinase complex with Cdc2/cyclin D in vitro." Plant Journal, May 1999. 18(3): p. 243–252.
Ramirez–Parra, E., et al., "The cloning of plant E2F, a retinoblastoma–binding protein, reveals unique and conserved features with animal G1/S regulators." Nucleic Acids Research, Sep. 1999. 27(17): p. 3527–3533.
Sekine, M., et al., "Isolation and characterization of the E2F–like gene in plants." FEBS Letters, Oct. 1999. 460(1): p. 117–122.
Soni, R., et al., "A family of cyclin D homologs from plants differentially controlled by growth regulators and containing the conserved retinoblastoma protein interaction motif." Plant Cell, 1995. 7(1): p. 85–103.
Xie, Q., et al., "Identification and analysis of a retinoblastoma binding motif in the replication protein of a plant DNA virus: Requirement for efficient viral DNA replication." EMBO (European Molecular Biology Organization) Journal, 1995. 14(16): p. 4073–4082.
Xie, Q., et al, "Plant cells contain a novel member of the retinoblastoma family of growth regulatory proteins." EMBO (European Molecular Biology Organization) Journal, 1996. 15(18): p. 4900–4908.
Fountain, M.D. et al., "Isolation of a Full–Length cDNA Encoding a Retinoblastoma (Accession No. Aj011681) Protein from Suspension Cultured Photoautotrophic Chenopodium rubrum L. Cells.", Plant Physiology, Jan. 1999, 119: 363.
AB012024 Pisum sativum mRNA, Plant RRB sequence published (so far) only in Genbank 2000.
AF133675 Populus tremula, Plant RRB sequence published (so far) only in Genbank 2000.
AF230739 Euphorbia esula, Plant RRB sequence published (so far) only in Genbank 2000.

\* cited by examiner

*Primary Examiner*—Ashwin Mehta
(74) *Attorney, Agent, or Firm*—Randall W. C. Chang; William C. Daubenspeck; Paul A. Gottlieb

(57) ABSTRACT

This invention provides methods and compositions for altering the growth, organization, and differentiation of plant tissues. The invention is based on the discovery that, in plants, genetically altering the levels of Retinoblastoma-related gene (RRB) activity produces dramatic effects on the growth, proliferation, organization, and differentiation of plant meristem.

6 Claims, No Drawings

RETINOBLASTOMA-LIKE RRB GENE OF ARABIDOPSIS THALIANA

CROSS-REFERENCE TO RELATED APPLICATIONS

This application claims the benefit of U.S. Provisional Application No. 60/125,229 filed Mar. 19, 1999, entitled "Alteration of Plant Meristem Function by Manipulation of the Retinoblastoma-like Plant RRB Gene", which is incorporated herein by this reference.

STATEMENT OF GOVERNMENT INTEREST

The United States Government has rights in this invention pursuant to Grant No. MCB9506985, between the National Science Foundation and the University of California, and Grant No. DE-FG03-88ER13882 between the U.S. Dept. of Energy and the University of California.

BACKGROUND OF THE INVENTION

The ability to control the size of plants and plant tissues is an enormously valuable tool. For example, for many agricultural crops, increasing the size of a plant or of a specific tissues within a plant would be of obvious commercial value. Currently, most attempts to increase plant size or yield are accomplished through traditional or marker-assisted breeding programs. Such methods have, however, failed to provide methods to directly control the size of plants or plant tissues.

Most cell proliferation in plants occurs in tissues called meristematic tissue. Several types of meristematic tissue exist in plants, including the shoot apical meristem, which gives rise to all aerial parts of the plant, the root apical meristem, which establishes the root system, and the vascular meristem, which provides lateral growth of the plant. While several genes are known to alter meristem fate, and thereby plant development, the mechanism by which they function is poorly understood. The products of the CLAVATA (CLV) and SHOOT MERISTEMLESS (STM1) genes of Arabidopsis, for example, encoding a receptor-kinase and homeodomain protein, respectively, appear to work antagonistically in a shoot meristem maintenance pathway involved in the partitioning of the central-peripheral zone (CZ-PZ) of the meristem. Other genes, such as ZWILLE (ZLL) and WUSCHEL (WUS), function early in embryonic development to specify the stem cells which will be maintained in the central zone of the shoot apical meristem. Other genes such as MGOUN1(MGO1) and MGOUN2 (MGO2) appear to function in the partitioning of cells from the PZ of the shoot apical meristem to leaf primordia or the inflorescence, often resulting in a fasciated meristem phenotype.

Plants containing mutations in the genes described above are defective in specific stages of meristem function and have well-characterized developmental phenotypes. As such, these genes are likely involved in the differentiation of meristematic cells, and are thus unlikely, by themselves, to provide tools to increase the size of plants or of plant tissues. Instead, it would be desirable to manipulate both the differentiation of meristematic cells as well as their growth and proliferation.

One potential method to alter the growth and/or proliferation of plant cells would be to modulate the activity of genes controlling these processes. For example, several groups have reported the cloning of at least a fragment of a Retinoblastoma-related protein in maize. See, e.g. Ach et al. (1997) Mol. Cell. Biol. 17:5077; Huntley et al. (1998) *Plant Mol. Biol.* 37:155; Grafi et al. (1996) *PNAS* 93:8962; Shen et al. (1994) Plant Mol. Biol. 26:1085; Xie et al. (1996) EMBO J 15:4900; and WO 97/47745. None of these studies, however, has investigated the function of RRB in proliferating, virus-free cells. Further, no studies have heretofore addressed the role of RRB in an intact plant. As well known to those of skill, only by examining the role of a protein in its normal environment, in an intact organism, can its true activity and/or function be determined.

Thus, the art lacks a good understanding of the function of RRB in plant cells and/or intact plants. Without this understanding, its use to control plant growth in an efficient manner is difficult if not impossible. The present invention addresses these and other needs.

SUMMARY OF THE INVENTION

This invention provides methods and compositions for altering the growth and differentiation of plant tissues. The invention is based on the discovery that, in plants, genetically altering the levels of Retinoblastoma-related gene (RRB) activity produces dramatic effects on the growth, proliferation, and differentiation of plant meristem. Altering the level of RRB activity in a plant tissue, therefore, can be used to specifically control the growth and/or differentiation of plant meristem, thereby controlling, e.g. the relative size and distribution of individual tissues in a plant.

In certain embodiments, this invention provides polynucleotides and polypeptides with plant RRB function. In one embodiment, the polynucleotide is as shown in SEQ ID NO:1 or SEQ ID NO: 9. In one embodiment, the polynucleotide encodes the polypeptide shown as SEQ ID NO:2, or fragments thereof. In a preferred embodiment, the polynucleotide encodes a fill-length RRB protein. However, truncated forms of RRB proteins can be used as well. In addition, mutated forms of the RRB proteins can be used, e.g. as dominant negative forms.

This invention also provides transgenic plants comprising RRB polynucleotides. In preferred embodiments, the RRB polynucleotides are operably linked to a promoter, such as an inducible or tissue-specific promoter.

This invention also provides methods for inhibiting or enhancing the growth of plant cells, plant tissues, or entire plants. In preferred embodiments, RRB activity is enhanced or inhibited in a plant tissue by expressing a wild type, .mutant, or truncated form of an RRB polynucleotide, or by expressing an inhibitor of RRB activity, e.g. a peptide that competitively binds RRB, thereby preventing its normal interaction with intracellular substrates.

The methods provided herein can also be used to alter the differentiation of a plant tissue. In preferred embodiments, the differentiation of a meristem is altered. For example, the present invention provides methods for modulating the RRB activity in an apical shoot meristem, thereby altering the size, organization, and/or differentiation of the meristem and, as a result, affecting the structure and/or number of, e.g., a leaf primordium or an inflorescence bolt. Increasing or decreasing RRB activity can be effected in a plant, a plant tissue, or a plant cell by expressing a wild type, mutant, or truncated form of an RRB polynucleotide, or by expressing a peptide inhibitor of RRB activity. Such RRB polynucleotides are preferably linked to promoters such as a tissue-specific or an inducible promoter.

DEFINITIONS

A "nucleic acid" refers to a single or double-stranded polymer of deoxyribonucleotide or ribonucleotide bases.

The term includes chromosomal DNA, self-replicating plasmids, infectious polymers of DNA or RNA and DNA or RNA that performs a primarily structural role. With respect to a naturally occurring nucleic acid that is "isolated" from its natural environment, the nucleic acid is substantially or essentially free from components which normally accompany or interact with it as found in its naturally occurring environment. However, an "isolated" nucleic acid can refer to a recombinantly or synthetically produced nucleic acid, that is identical or altered from the naturally occurring nucleic acid sequence. In addition, an "isolated nucleic acid" can comprise naturally occurring nucleotides or can comprise any nucleotide derivative or analog, e.g. labeled nucleotides, that can be incorporated into a polynucleotide chain. Any aspect of the polynucleotide chain can be altered, such as the base, sugar, or phosphate backbone.

The term "promoter" refers to regions or sequence located upstream and/or downstream from the start of transcription and which are involved in recognition and binding of RNA polymerase and other proteins to initiate transcription. A "plant promoter" is a promoter that works in plants, e.g. CaMV 35S. A "tissue-specific promoter" is a promoter capable of initiating transcription in a certain tissue of a plant. A "tissue specific promoters" can comprise a naturally occurring promoter that drives the expression of a gene in one or more specific tissues, or can comprise modified, truncated, or otherwise modified derivatives of naturally occurring promoters, or can comprise a synthetic promoter with the desired properties. A "tissue specific promoter" can drive the expression of a gene in one or more tissues, and throughout the entire tissue or only in a subset of the tissue. In addition, a "tissue-specific promoter" can drive gene expression in a tissue throughout the life of a plant, or transiently at one or more times during the life of the plant.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnospenms, ferns, and multicellular algae. It includes plants of a variety of ploidy levels, including aneuploid, polyploid, diploid, haploid and hemizygous.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

As used herein, the term "RRB polynucleotide" refers to any polynucleotide encoding a polypeptide with RRB activity, and which encodes a polypeptide with at least about 50% sequence identity to the exemplified sequences provided herein. The RRB polypeptides encoded by RRB polynucleotides have at least about 50%, 60%, 70%, 80%, 90% or higher sequence identity at the deduced amino acid level relative to the exemplary RRB polynucleotide sequences provided herein. "RRB polynucleotide" includes reference to nucleic acids of at least about 20, 30, 40, or 50 nucleotides in length, more preferably about 100, 200, 500, 1000, 2000, 5000 or more nucleotides. Thus, an "RRB polynucleotide" can be an RRB gene or a subsequence thereof.

"RRB activity" refers to one or more biochemical or genetic properties of an RRB polynucleotide or polypeptide. For example, when expressed in cells or tissues of a plant, an RRB polynucleotide can affect the growth, proliferation, and/or differentiation of plant cells and tissues, resulting in the phenotypes described herein. In addition, RRB can bind to a number of heterologous proteins, such as E2F, D-type cyclins, or viral proteins such as large-T antigen or EIA, or the geminivirus protein RepA. Often, such proteins will bind RRB through an LXCXE motif. Accordingly, RRB activity can be assessed based on binding to any LXCXE-motif containing polypeptide. Any of these activities, inter alia, can be monitored or modified according to the present invention.

An "inhibitor of RRB activity", as used herein, refers to any material that results in the decrease of RRB activity. Such molecules can include expressible forms of RRB polynucleotides, such as antisense RRB polynucleotides, RRB polynucleotides used to inhibit by co-suppression, dominant-negative forms of RRB such as truncated or mutated forms of RRB, as well as other expressible inhibitors such as peptide inhibitors of RRB or anti-RRB ribozymes. In addition, an "inhibitor of RRB activity" can include any material that can be used to decrease RRB activity, such as molecules that inhibit the activity, expression, or stability of RRB polynucleotides or polypeptides.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henioff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in *Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising RRB nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency. In preferred embodiments, stringent. hybridization conditions for screening cDNA libraries and/or for Southern blot hybridizations include:
Hybridization at 55° C. in the following:
  0.75 M NaCl
  5 mM EDTA pH 8
  0.15 M Tris HCl pH 8
  2.75 mM tetra sodium pyrophospate
  0.1% Ficoll
  0.1% polyvinyl pyrrolidone
  0.1% BSA
  10% Dextran sulphate
  0.1% SDS
  0.05 mg/ml herring sperm DNA
  Washing in 2×SSC, 0.1% SDS at 55° C., using, e.g. an RRB cDNA as a probe for hybridization.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DETAILED DESCRIPTION OF THE INVENTION

This invention provides methods of directly controlling the size and/or differentiation state of plants, plant tissues, or plant cells. This invention is based on the surprising discovery that, in intact plants, alterations in RRB levels dramatically affect the growth, organization, as well as differentiation of specific tissues. By specifically increasing or decreasing the level of RRB in cells within an intact plant, therefore, it is possible to increase or decrease the size of the tissue or plant comprising the cells. When directed to specific tissues within a plant, it is thus possible to specifically and controllably alter the growth and/or differentiation of the tissue.

I. RRB

Any of a number of RRB sequences can be used in the present invention.

RRB sequences can be used from any monocotyledonous or dicotyledonous plant, such as Arabidopsis, *Zea mays*, Chenopodium, and tobacco. In addition, RRB homologs from animals, such as from mammals, fish, birds, insects, etc. can be used. In preferred embodiments, an RRB nucleotide sequence will be used that will hybridize, under low to moderate stringency, to SEQ ID NO:1, 3, 5, 7, or 9, or which is substantially identical to all or part of SEQ ID NO:1, 3, 5, 7, or 9. Also preferred is the use of RRB polypeptides substantially similar to all or part of SEQ ID NO:2, 4, 6, or 8. The present invention can be used with full-length, truncated, wild type, or mutated forms of RRB, as described infra.

Typically, the RRB sequences will include one or more functional domains characteristic of RRB sequences, such as the A or B pocket, one or more protein or protein-motif binding domains, e.g. an LXCXE motif binding domain, and phosphorylation sites. In addition, the N-terminal 130 amino acids, or 383 5' nucleotides, of the Arabidopsis sequence, which are not found in *Zea mays*, can be used. Such Arabidopsis-specific sequences can readily be identified by comparing an Arabidopsis sequence, e.g. SEQ ID NO:1, with, e.g. a *Zea mays* sequence as shown in SEQ ID NO:3, 5, or 7. RRB sequences can be isolated from any natural source, can be derived from a natural source, i.e. a mutated or truncated derivative, or can be synthesized de novo. Methods for purifying, mutating, and recombinantly altering nucleic acids are well known in the art, and can be found in any of a multitude of guides, such as Sambrook et al., (1989) and Ausubel et al. (1999).

II. Altering RRB Expression and/or Activity in Plant Tissues

The present invention can be used to alter the growth, organization, and/or differentiation of any of a number of plant tissues. Typically, the tissues will comprise meristematic tissue, including root meristem, shoot apical meristem, vascular meristem, or endosperm. In certain embodiments, RRB activity may be modulated in non-meristematic tissue, e.g. to affect the differentiation of the tissue or, e.g. to promote proliferation in normally non-proliferating cells. Accordingly, the present methods can be used to affect the growth and/or differentiation of any part of a plant, including roots, stems, leaves, flowers, seed, fruit, tubers etc., as well as any structure within one of these parts, e.g. bracts, sepals, petals, stamens, carpels, anthers, ovules, embryos, endosperm, and seed coat).

Any of these tissues can be targeted individually or in combination, e.g. using one or more tissue specific promoters such as leaf-specific promoters, flower meristem-specific promoters, endosperm-specific promoters, root-specific promoters, etc. Also, the tissues can be targeted at all times during the life of the plant, e.g. using a constitutive promoter, or transiently, e.g. using a transiently active or an inducible promoter. It will be appreciated that, e.g. using multiple expression constructs, RRB activity can be simultaneously increased in one tissue and decreased in another in a single plant, thereby altering the relative sizes of the tissues within a plant. For commercial crops, such methods would allow the relative increase in the yield of valuable tissues, and the decrease in size of unwanted tissues.

These methods can be used to enhance and/or inhibit the growth and differentiation of plant cells. Further, we have discovered a relationship between the amount of increase or decrease in the level of RRB activity and the degree to which growth, organization, and/or differentiation is affected. For example, in a transgenic plant with an RRB polynucleotide under the control of an inducible promoter, adding a small amount of the inducing agent results in a mild effect on growth, organization, and/or differentiation, whereas adding a substantial amount of the agent results in dramatic changes in the rate or level of growth, organization and/or differentiation. Accordingly, the present invention can be used to alter the degree to which a plant tissue grows, organizes, and/or differentiates, e.g. by using a variable amount of an inducing agent or by using promoters of various strengths.

In certain embodiments, the level of RRB activity will be altered alone, i.e. no other cellular moieties will be manipulated. In other embodiment, however, RRB levels can be altered in conjunction with other cellular components. For example, other regulators of cell growth, cell proliferation, or cellular differentiation may be altered to enhance or attenuate the effects of the altered RRB levels. In certain embodiments, genes involved in meristem formation and/or differentiation may be used, e.g. CLV, STM1, ZLL, WUS, MGO1, or MGO2. For example, a gene promoting meristem formation may be used to increase the amount of meristem, which can be increased further by, e.g. modulating the levels of RRB in the meristem. Finally, the enlarged meristem can subsequently be induced to differentiate by further altering RRB activity in the cells.

A. Increasing RRB Activity or RRB Gene Expression

Any of a number of means well known in the art can be used to increase RRB activity in plants. Increased RRB activity can be used to, e.g. modulate the growth of plant tissues, modulate the organization of plant tissues, and/or modulate the differentiation of the tissues. In a preferred embodiment, increasing RRB. activity in cells within a plant or a plant tissue results in a decrease in the size of the plant or plant tissue. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, one or more RRB genes can be expressed constitutively (e.g., using a constitutive promoter).

1. Increasing Expression of RRB Polynucleotides

Isolated sequences prepared as described herein can be used to introduce expression of a particular RRB nucleic acid to increase gene expression using methods well known to those of skill in the art. Preparation of suitable constructs and means for introducing them into plants are described below.

One of skill will recognize that the polypeptides encoded by the genes of the invention, like other proteins, have different domains that perform different functions. Thus, the gene sequences need not be full length, so long as the desired functional domain of the protein is expressed. For example, RRB can bind to various proteins, such as E2F, D-type cyclins, EIA, large T-antigen, and other viral proteins, and has multiple conserved domains, such as the A and B pocket domains and conserved phosphorylation sites. Any of these binding sites or conserved regions may be used in the present invention.

Modified protein chains can also be readily designed utilizing various recombinant DNA techniques well known to those skilled in the art and described in detail below. For example, the chains can vary from the naturally occurring sequence at the primary structure level by amino acid substitutions, additions, deletions, and the like. These modifications can be used in a number of combinations to produce the final modified protein chain.

In certain embodiments, modified forms of RRB will be used that have increased RRB activity in vivo. For example, creating forms of RRB that cannot be inhibited by phosphorylation will create a hyperactive form of RRB. Additional hyperactive forms can be readily identified, e.g. by screening for modified forms of RRB with an enhanced ability to inhibit the cell cycle or to promote differentiation.

RRB polynucleotide expression can be increased throughout a plant, in one or more tissues or cells of a plant, and constitutively or transiently. Such expression patterns can be achieved using any of a variety of promoters, including endogenous RRB promoters, heterologous promoters, constitutive promoters, tissue-specific promoters, and inducible promoters.

2. Modification of Endogenous RRB Genes to Increase RRB Activity

In certain embodiments of this invention, endogenous RRB may be modified by introduction of genetic mutations. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used. Methods for screening for those plants having the desired genetic mutation in the RRB gene are well known in the art.

In applying homologous recombination technology to the genes of the invention, mutations in selected portions of an RRB gene sequence (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255 (1995) are conveniently used to increase the efficiency of selecting for altered RRB gene expression in transgenic plants. The mutated gene will interact with the target wild-type gene in such a way that homologous recombination and targeted replacement of the wild-type gene will occur in transgenic plant cells, resulting in increased RRB activity.

3. Other Means for Increasing RRB Activity

One method to increase RRB expression is to use "activation mutagenesis" (see, e.g. Hiyashi et al. *Science* 258:1350–1353 (1992)). In this method an endogenous RRB gene can be modified to be expressed constitutively, ectopically, or excessively by insertion of T-DNA sequences that contain strong/constitutive promoters. Screening methods well known in the art maybe used to screen for those plant lines having T-DNA inserted upstream of the endogenous RRB gene. As explained below, preparation of transgenic plants overexpressing RRB can also be used to increase RRB expression. Activation mutagenesis of the endogenous RRB gene will give the same effect as overexpression of the transgenic RRB nucleic acid in transgenic plants. Alternatively, an endogenous gene encoding an enhancer of RRB activity or expression of the endogenous RRB gene can be modified to be expressed by insertion of T-DNA sequences in a similar manner and RRB activity can be increased.

Another strategy to increase RRB expression can involve the use of dominant hyperactive mutants of RRB by expressing modified RRB transgenes. For example expression of modified RRB with a defective domain that is important for interaction with a negative regulator of RRB activity can be used to generate dominant hyperactive RRB proteins. Alternatively, expression of truncated RRB proteins which have only a domain that interacts with a negative regulator can titrate the negative regulator and thereby increase endogenous RRB activity. Use of dominant mutants to hyperactivate target genes is described, e.g., in Mizukami et al. *Plant Cell* 8:831–845 (1996).

B. Inhibition of RRB Activity or Gene Expression

As explained above, RRB activity is important in controlling the growth and differentiation of cells. Inhibition of RRB gene expression activity can be used, for instance, to alter cell growth and/or proliferation, to modulate tissue organization, and/or to modulate differentiation of cells within a tissue or plant. In a preferred embodiment, decreasing RRB activity in cells of a plant or a plant tissue results in an increase in the size of the plant or plant tissue. In particular, targeted expression of RRB nucleic acids that inhibit endogenous gene expression (e.g., antisense or co-suppression) can be used.

1. Inhibition of RRB Gene Expression

The nucleic acid sequences disclosed herein can be used to design nucleic acids useful in a number of methods to inhibit RRB or related gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (Limerick) 105: 125–149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. pp. 181–238; Heiser et al. *Plant Sci. (Shannon)* 127: 61–69 (1997)) and by preventing the accumulation of mRNA which encodes the protein of interest, (see, Baulcombe *Plant Mol. Bio.* 32:79–88 (1996); Prins and Goldbach *Arch. Virol.* 141: 2259–2276 (1996); Metzlaff et al. *Cell* 88: 845–854 (1997), Sheehy et al., *Proc. Nat. Acad. Sci. USA*, 85:8805–8809 (1988), and Hiatt et al., U.S. Pat. No. 4,801,340).

The nucleic acid segment to be introduced generally will be substantially identical to at least a portion of the endogenous RRB gene or genes to be repressed. The sequence, however, need not be perfectly identical to inhibit expression. The vectors of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress RRB gene expression. The targets can include, for instance, the coding regions, introns, sequences from exon/intron junctions, 5' or 3' untranslated regions, and the like.

Another well-known method of suppression is sense co-suppression. Introduction of nucleic acid configured in the sense orientation has been recently shown to be an effective means by which to block the transcription of target genes. For an example of the use of this method to modulate expression of endogenous genes (see,. Assaad et al *Plant Mol. Bio.* 22: 1067–1085 (1993); Flavell *Proc. Natl. Acad. Sci. USA* 91: 3490–3496 (1994); Stam et al. *Annals Bot.* 79: 3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants that over-express the introduced sequence. A higher identity in a sequence shorter than full-length compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

Oligonucleotide-based triple-helix formation can also be used to disrupt RRB gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al *FASEB J.* 9:1288–1296 (1995); Giovannangeli et al. *Biochemistry* 35:10539–10548 (1996); Chan and Glazer *J. Mol. Medicine (Berlin)* 75: 267–282 (1997)). Triple helix DNAs can be used to target the same sequences identified for antisense regulation.

Catalytic RNA molecules or ribozymes can also be used to inhibit expression of RRB genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick, *Nature* 365:448–451 (1993); Eastham and Ahlering, *J. Urology* 156:1186–1188 (1996); Sokol and Murray, *Transgenic Res.* 5:363–371 (1996); Sun et al., *Mol. Biotechnology* 7:241–251 (1997); and Haseloff et al., *Nature*, 334:585–591 (1988).

2. Modification of Endogenous RRB Genes

Methods for introducing genetic mutations described above can also be used to select for plants with decreased RRB expression.

3. Other Methods for Inhibiting RRB Activity

RRB activity may be modulated by eliminating the proteins that are required for RRB cell-specific gene expression. Thus, expression of regulatory proteins and/or the sequences that control RRB gene expression can be modulated using the methods described here.

Another strategy is to inhibit the ability of a RRB protein to interact with itself or with other proteins. This can be achieved, for instance, using antibodies specific to RRB. In this method cell-specific expression of RRB-specific antibodies is used to inactivate functional domains through antibody:antigen recognition (see, Hupp et al., *Cell* 83:237–245 (1995)). Interference of activity of a RRB interacting protein(s) can be applied in a similar fashion.

Alternatively, dominant negative mutants of RRB can be prepared by expressing a transgene that encodes a truncated RRB protein. Use of dominant negative mutants to inactivate target genes in transgenic plants is described in Mizukami et al., *Plant Cell* 8:831–845 (1996). In a preferred embodiment, an RRB polypeptide with a mutation that prevents binding of RRB to heterologous proteins, e.g. a mutation in a conserved cysteine residue (corresponding to C706 of human RB), is expressed in a cell. With respect to the Arabidopsis cDNA shown as SEQ ID NO:1, the alteration comprises a cysteine to phenylalanine substitution, resulting from a G to T change at position 2363 bp. In particularly preferred embodiments, such mutated or truncated RRB proteins are expressed at a level at least as high as that of the endogenous RRB protein.

Another approach to inhibit RRB activity is through the use of peptide inhibitors of RRB activity. Such inhibitors may be derived from naturally occurring proteins, e.g. RRB binding proteins. For example, a fragment of E2F that competitively binds RRB and prevents it from binding to full length E2F may be expressed in a cell. Also, a peptide include an LXCXE motif can be used, thereby competitively blocking the binding of proteins such as D-type cyclins to RRB. However, any peptide with the ability to inhibit RRB activity, by interacting directly with RRB itself or with a substrate of RRB, can be used. Such peptides can be easily identified, for example, by generating a library of peptide molecules and screening the library for peptides with the ability to bind to and/or inhibit RRB in vitro or in vivo.

In certain embodiments, a non-peptide inhibitor of RRB can be used. Such inhibitors can be any molecule or treatment that reduces RRB activity in a cell. Such molecules can include organic compounds including nucleic acids, nucleotides, amino acids, carbohydrates, fats, waxes, hormones, etc., or any inorganic compounds. Any compound can be screened for the ability to bind to and/or inhibit RRB activity, in vitro or in vivo. In addition, any non-molecular treatment, e.g. temperature, electromagnetic radiation, motion, etc. that affects RRB activity can be employed.

III. Isolation and Manipulation of RRB Polynucleotides and Polypeptides

A. Purification of RRB Polypeptides

Either naturally occurring or recombinant RRB polypeptides can be purified for use in functional assays, e.g. protein binding assays. Naturally occurring RRB polypeptides can be purified, e.g., from plant tissue and any other source of a RRB homolog. Recombinant RRB polypeptides can be purified from any suitable expression system.

The RRB polypeptides may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant RRB polypeptides are being purified. For example, proteins having established molecular adhesion properties can be reversible fused to the RRB polypeptides. With the appropriate ligand, the RRB polypeptides can be selectively adsorbed to a purification column and then freed from the column in a relatively pure form. The fused protein is then removed by enzymatic activity. Finally the RRB polypeptides could be purified using immunoaffinity columns.

B. Isolation of RRB Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y. (1989) or Current Protocols in Molecular Biology Volumes 1–3, John Wiley & Sons, Inc. (1994–1998).

The isolation of RRB nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaves, and a cDNA library which contains a RRB gene transcript is prepared from the mRNA. Alternatively, cDNA may be prepared from mRNA extracted from other tissues in which RRB genes or homologs are expressed.

The cDNA or genomic library can then be screened using a probe based upon the sequence of a cloned RRB gene disclosed here. Probes may be used to hybridize with genomic DNA or cDNA sequences to isolate homologous genes in the same or different plant species. Alternatively, antibodies raised against a RRB polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of RRB genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), *Academic Press*, San Diego (1990). Appropriate primers and probes for identifying RRB sequences from plant tissues are generated from comparisons of the sequences provided herein (e.g. SEQ ID NO: 1, SEQ ID NO:3, SEQ ID NO:5, SEQ ID NO:7, etc.).

Polynucleotides may also be synthesized by well-known techniques, as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

C. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S and 19S transcription initiation regions; the full-length FMV transcript promoter (Gowda et al., *J Cell Biochem* 13D:301; the 1'- or 2'-promoter derived from T-DNA of *Agrobacterium tumafaciens*, and other transcription initiation regions from various plant genes known to those of skill. Such promoters and others are described, e.g. in U.S. Pat. No. 5,880,330. Such genes include for example, ACT11 from Arabidopsis (Huang et al. *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from Brassica napus (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of RRB nucleic acid in a specific tissue, organ or cell type (i.e. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. Numerous inducible promoters are known in the art, any of which can be used in the present invention. Such promoters include the yeast metallothionine promoter, which is activated by copper ions (see, e.g. Mett et al. (1993) PNAS 90:4567), the dexamethasone-responsive promoter, In2-1 and In2-2, which are activated by substituted benzenesulfonamides, and GRE regulatory sequences, which are glucocorticoid-responsive.

Tissue-specific promoters can be inducible. Similarly, tissue-specific promoters may only promote transcription within a certain time frame of developmental stage within that tissue. Other tissue specific promoters may be active throughout the life cycle of a particular tissue. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in leaves, roots or flowers are useful for the growth, proliferation, and/or differentiation of those organs. For expression of a RRB polynucleotide in the aerial vegetative organs of a plant, photosynthetic organ-specific promoters, such as the RBCS promoter (Khoudi, et al., *Gene* 197:343, 1997), can be used. Root-specific expression of RRB polynucleotides can be achieved under the control of the root-specific ANR1 promoter (Zhang & Forde, *Science*, 279:407, 1998). Other suitable tissue specific promoters include the cdc2a and cyc07 promoters, the histone promoter, the cinnamyl alcohol dehydrogenase (CAD) promoter, the mustard CHS1 promoter, the bean grp 1.8 promoter, the PAL1 promoter, the chalcone synthase A promoter, the UFO promoter, and others. In preferred embodiments, a promoter will be used that drives RBB expression specifically in a meristem. In preferred embodiments, an RRB promoter will be used. For example, the RRB promoter shown in SEQ ID NO:9 (e.g approximately base pairs 1–543) can be used to drive expression of operably linked sequences in meristematic and other tissues in Arabidopsis or any type of plant.

In addition, the promoter shown in SEQ ID NO:9 (e.g. approximately base pairs 1 to 543 or, e.g. 1–1000) can be used to drive the expression of heterologous genes in meristematic tissue. RRB promoters can be used to drive the expression of any heterologous gene whose expression in meristematic tissue is desired. For example, cell cycle-related genes such as cyclins, Cdks, E2F, DP, p53, Cdc25, CKIs, or any derivative or variation thereof, can be used, as can developmental genes such as CLV, STM1, ZLL, WUS, MGO1, or MGO2.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin; G418, bleomycin, hygromycin, or herbicide resistance, such as resistance to chlorosulfuron or Basta.

IV. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo. J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant. Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of RRB mRNA or protein in transgenic plants. Means for detecting and quantitating mRNAs or proteins are well known in the art.

EXAMPLES

The full-length Arabidopsis thaliana Rb (AtRRB) cDNA was cloned into plant expression cassettes behind a dexamethasone-inducible promoter (DEX-inducible plasmid pTA7002) to manipulate ectopic expression (AtRRB-OE) of the AtRRB gene. A mutated version of the AtRRB cDNA containing a cystidine to phenylalanine substitution resulting from a G to T change at position 2363 bp was also cloned into a plant expression cassette (AtRRBcys-OE). By analogy to metazoan Rb-like proteins, the protein encoded by AtRRBcys would be altered in structure and function and is predicted to act as a dominant negative mutation when ectopically expressed.

Numerous phenotypic alterations were observed in transgenic lines, including enlargement of the inflorescence bolt, or formation of multiple meristems at the shoot apex. Other phenotypic alterations include delayed leaf emergence, altered leaf morphology (with regard to degree of development, shape and fused organs), or terminal flower formation. A subset of transgenic lines show a complete loss of shoot and root apical meristem activity. Our results document a key role for the product of the plant RRB gene in meristem differentiation, organization, and the meristematic cell cycle. The plant RRB gene is therefore a key target for functional manipulations to alter cell cycle regulation, apportioning of cells to primordia, and cellular differentiation in shoot and root apical meristems.

Numerous phenotypes were observed in most of the transgenic lines in the uninduced condition, i.e. in the absence of dexamethasone (the DEX—inducible promoter system is known to be "leaky" in vivo). Phenotypes were typically enhanced following induction of the promoter with dexamethasone. These results demonstrate that we can modify expression of the transgenes and phenotypic responses. Of the different phenotypes obtained in the DEX-AtRRB-OE and DEX-AtRRBcys-OE transgenic lines, the most penetrant phenotypes observed are in the impaired ability of the meristem to (1) generate leaf primordia and (2) to maintain a proper size and/or organization, as observed by severely delayed leaf emergence and fasciation of the inflorescence bolt, respectively. These phenotypes are reminiscent o *Arabidopsis thaliana* mgo mutants, which have a similar phenotype including delayed emergence of leaves and an enlarged shoot apical meristem, observed as fasciation. These results suggest that one function of AtRRB is the removal of cells from the PZ of the shoot apical meristem and in the differentiation of the leaf primordia.

Other phenotypes which occur in the most transgenic lines to different degrees of penetrance include (1) the development of adventitious meristems and/or splitting of the shoot apical meristem, (2) the production of leaves which are altered in shape or are fused, and (3) the inability of the inflorescence meristem to maintain a population of undifferentiated cells which results in the production of a terminal flower. These phenotypes support the conclusion that defects in shoot apical and inflorescence meristem formation, maintenance or function are obtained by manipulating AtRRB expression in vivo.

Transgenic lines expressing DEX-AtRRB-OE that have severe phenotypes in the uninduced condition showed an extreme phenotype when the DEX-inducible promoter was activated. Shoot and root apical meristem function was completely attenuated. Primary and secondary roots and primary leaves did not form, and the plants died with expanded but small cotyledons. This severe phenotype showed a penetrance of 100% in a population of hemizygous and homozygous individuals of two lines and slightly less in a third line. The complete loss of shoot and root meristem function in these lines following DEX induction confirms that AtRRB has a key role in meristem formation and maintenance, including control of cell cycle activity within proliferating populations of meristem cells and/or organ primordia differentiation.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

SEQ ID NO:1—Arabidopsis RRB1 cDNA Sequence

GAAGTCAGGTGAAGATAGAGAGAGA-
CACTGAGAGGAGGGAAAATTTGT
AGGGTTTTCGGAGATCTCTGTGATTC-
CTCTGAATTTGTCGAATTTTTTCGA GGAGGCGT-
TAGAAGTCGGGCTTCTTAAAATCA-
GATCTTCTGCTCAGGCT
TTAATCGGCGACGTCTGGTATTGG-
GATCTGTGACACAAAAAGCTGCGTTG GAGAC-

TATGGAAGAAGTTCAGCCTCCAGTGAC-
CCCGCCCATTGAACCAA
ATGGGAAAAGAAGCGAAGCCTCTCTCT-
TGGACATATGCGAGAAAGTTCT GTCTCT-
TGATGGGAGCACTTGCGAT-
GAAGCTTTGAAGTTGTTTACAGAAA
CCAAACGAATTTTGTCAGCAAGCAT-
GTCTAACATTGGAAGTGGAACGCG GGAAGAAG-
TAGAGAGGTTCTGGTTTGCGTTTAT-
TCTCTATTCAGTGAAGA
GGCTTAGTGTGAGAAAAGAAGCGGATG-
GTCTGTCAGTGTCTGGTGATAA TGAGTTTAATC-
TATGTCAGATACTGAGGGCTCT-
GAAGCTAAATATTGTGG
ATTTTTTTAAAGAGTTACCT-
CAGTTTGTGGTCAAGGCTGGATCTGTACTG GGT-
GAACTTTACGGCGCAGACTGGGAGAACA-
GACTTCAGGCAAAGGAGG
TGCAGGCTAACTTTGTGCATCTTAGCCT-
TCTAAGCAAATACTACAAACGT GGGTTCCGG-
GAATTCTTTTTGACATATGATGCAAACG-
CAGAAAAGAACTC
AGCAAACTCTTCTACCTATTTGCTGGAT-
AGTTATCGTTTTGGATGGCTACT CTTTTTG-
GCACTCCGAAACCATGCGTTTAGTC-
GATTTAAGGACCTCGTGA
CATGCTCAAATGGCGTAGTTTCTATAT-
TGGCTATTTTGATCATACATGTTC CTTGTCGGTT-
TAGAAATTTCAGCATCCAAGATTCT-
TCTCGCTTTGTTAAGA
AAGGTGACAAAGGTGTAGACTTGGTTG-
CATCACTTTGCAAGATATATGAC GCCTCAGAA-
GATGAGTTGAGGATAGTAATTGACAAG-
GCAAATAATTTGG
TAGAAACCATACTGAAGAAAAAGC-
CATCTCCAGCATCTGAGTGCCAAAC TGA-
CAAGCTAGATAATATTGACCCAGATG-
GCTTGACCTACTTTGAGGATT
TACTGGAAGAGACGTCCATCTCAAC-
TAGCTTAATTACACTTGAAAAGGAT TACTAT-
GATGGTAAAGGCGAACTTGATGAGAGGG-
TATTCATCAATGAAG
AGGATAGCTTACTTGGATCTGGAAGCT-
TATCTGCAGGAGCTGTTAATATT ACTGGTGTTAA-
GAGGAAAATTGATGCTTTGAGCTCACCT-
GCAAGGACATT
TATAAGCCCACTTTCTCCTCAT-
AAGTCGCCTGCTGCTAAGACAAATGGTA
TTAGCGGTGCTACCAAGTTGGCAGCAA-
CACCAGTGAGCACAGCAATGAC AACTGC-
CAAGTGGCTCAGGACTGTCATATC-
CCCGCTTCTGCCAAAACCTT
CTCCTGGGTTGGAACATTTCCTTAAAT-
CATGTGATAGGGATATAACAAAT GACGTCACAC-
GAAGAGCACACATAATATTGGAAGC-
TATTTTCCCAAATA
GTTCCCTTGGTGCCCAATGTGGAGGTG-
GAAGTTTGCAAGCTGTTGACCTG ATGGATGA-
CATATGGGCAGAGCAGCGCAGATTA-
GAAGCTTGTAAGTTAT
ACTACAGAGTTCTTGAGGCAATGTG-
TAAAGCAGAAGCTCAGATTTTGCAT
GCAAATAATCTGAACTCTTTATTGA-
CAAATGAGAGGTTCCATAGATGCAT GCTTGCT-
TGCTCAGCTGAATTGGTACTGGCTAC-
CCACAAAACAATTACAA
TGTTGTTCCCAGCTGTTCTGGAGAG-
GACTGGGATCACAGCCTTTGATCTC AGCAAGG-
TAATTGAGAGTTTCATACGACATGAA-
GATTCTCTGCCTAGAG
AGTTGAGACGACATCTGAATTCACTG-
GAGGAACGGCTTCTAGAGAGTAT GGTATGG-
GAGAAAGGCTCTTCAATGTACAAT-
TCTCTGATTGTTGCCAGGC
CATCGCTTGCATTGGAGATAAAT-
CAGCTCGGTTTACTAGCTGAACCAATG
CCATCTCTGGATGCAATCGCAGCACT-
TATTAATTTCTCTGACGGAGCAAA TCATGCAT-
CATCTGTACAAAAGCATGAAACTTGTC-
CAGGACAAAATGGG
GGGATTAGATCGCCCAAAAGATTATG-
TACTGATTACCGCAGCATTCTAGT TGAACGCAAT-
TCCTTTACATCACCAGTAAAG-
GATCGTCTGTTGGCCTTAG
GCAACGTTAAATCCAAGATGCTGCCAC-
CTCCGTTGCAGTCTGCATTTGCC AGCCCAA-
CACGGCCCAACCCAGGAGGTGGAG-
GAGAAACTTGTGCAGAA
ACTGGAATCAATATTTTCTTCACAAA-
GATTAATAAATTGGCTGCTGTAAG AATCAATG-
GAATGGTGGAAAGACTACAACTTTCA-
CAGCAAATAAGGGAG
AGTGTGTATTGTTTCTTCCAACATG-
TACTTGCTCAGCGGACTTCTCTTTTA TTCAGTC-
GACACATTGACCAGATCATTCTCTGT-
TGCTTCTACGGAGTGGC
CAAGATATCCCAAATGAGCCT-
GACTTTCAGGGAAATCATATACAACTACC
GGAAGCAACCACAGTGTAAACCATT-
AGTTTTCCGCAGCGTTTATGTGGAT GCGTTA-
CAATGTCGCCGTCAAGGGAGAATAGGGC-
CAGATCATGTTGACA
TCATCACATTCTACAATGAAATATTTAT-
TCCTGCCGTAAAGCCGCTGCTG GTGGAGCTAG-
GTCCTGTAAGAAACGACCGGGCTGTG-
GAAGCCAATAATA
AGCCTGAAGGTCAATGTCCCGGATCGC-
CAAAGGTGTCTGTGTTTCCAAGT GTTCCAGA-
CATGTCCCCTAAAAAAGTATCTGCAGTG-
CACAATGTTTATGT
TTCTCCTCTTCGGGGATCAAAGATGGAT-
GCTCTTATTTCACACAGTACAA AGAGTTACTAT-
GCTTGTGTTGGAGAGTACACATGCT-
TACCAGAGCCCT
TCAAAGGACCTATCTGCCATCAACAAC-
CGCTTGAACAACAGCAGCAGCA ACCGCAAGAG-
GACGCTAAACTTTGACGCAGAAGCAGG-
GATGGTCAGCGA
TTCCATGGTAGCAAATAGCCTTAACCTC-
CAAAACCAAAATCAAAACCAA AATGGAAGC-
GATGCATCGTCCTCAGGTGGTGCCGCAC-
CCCTTAAAACCG
AGCCAACAGATTCATAGATATCTCTCTC-
TACTTGCTACACCAACTTCTCTT CAGTTATAG-
CATCTGTAAATCCTTATGTTGCA-
GAGTTTGCTTTTATGTTTA
GCTTTCTAGTTTATAGTGATCACCTCAG-
GCTATGAGCGGATGGATCCCTT TAT-
TGTTTCTTTTTTCTTTTTTTATCTTAGT-
TAAGTCAGTCTTAATAAGCAT
TAATAAATGTCTTTTTCTTGT-
TCAAAAAAAAAAAAAAAAA

SEQ ID NO:2—Arabidopsis RRB1 Polypeptide
Sequence

MEEVQPPVTPPIEPNGKRSEASLLDI-
CEKVLSLDGSTCDEALKLFTETKRILSA SMSNIGS-

GTREEVERFWFAFILYSVKRLS-
VRKEADGLSVSGDNEFNLCQILRA
LKLNIVDFFKELPQFVVKAGSVLGE-
LYGADWENRLQAKEVQANFVHLSLLS KYYKRG-
FREFFLTYDANAEKNSANSSTYLLDSYR-
FGWLLFLALRNHAFSRF
KDLVTCSNGVVSILAILIIHVPCRFRNF-
SIQDSSRFVKKGDKGVDLVASLCKIY DASEDEL-
RIVIDKANNLVETILKKKPSPASECQTD-
KLDNIDPDGLTYFEDLLE
ETSISTSLITLEKDYYDGKGELDER-
VFINEEDSLLGSGSLSAGAVNITGVKRKI DALSS-
PARTFISPLSPHKSPAAKTNGISGATK-
LAATPVSTAMTTAKWLRTVIS
PLLPKPSPGLEHFLKSCDRDITNDVTR-
RAHIILEAIFPNSSLGAQCGGGSLQAV DLMDDI-
WAEQRRLEACKLYYRVLEAMCKAEAQIL-
HANNLNSLLTNERFHR
CMLACSAELVLATHKTITMLFPAVLERT-
GITAFDLSKVIESFIRHEDSLPRELR RHLNSLEER-
LLESMVWEKGSSMYNSLIVARPSLA-
LEINQLGLLAEPMPSLDAI
AALINFSDGANHASSVQKHETCPGQNG-
GIRSPKRLCTDYRSILVERNSFTSPV KDRLLALGN-
VKSKMLPPPLQSAFASPTRPNPGGGGET-
CAETGINIFFTKINKL
AAVRINGMVERLQLSQQIRESVYCFFQH-
VLAQRTSLLFSRHIDQIILCCFYGV AKISQMSLT-
FREIIYNYRKQPQCKPLVFRS-
VYVDALQCRRQGRIGPDHVDIIT
FYNEIFIPAVKPLLVELGPVRN-
DRAVEANNKPEGQCPGSPKVSVFPSVPDMSP
KKVSAVHNVYVSPLRGSKMDALISH-
STKSYYACVGESTHAYQSPSKDLSAIN NRLNNSSS-
NRKRTLNFDAEAGMVSDSMVANSLNLQN-
QNQNQNGSDASSSG GAAPLKTEPTDS

SEQ ID NO:3—Zea mays RRB1 cDNA

TCATCTCCCGTTCACCCCGCGGGCG-
CAGGGCGCGCTCTCTCCTCGTGGCG ATCGC-
CGACCGTAGCGGCCGCTGC-
CCGGGTTTTCGTCGGCCGCTTCGCCA
TGTCTTCGCTGGACCCTTCGCCAGCGAC-
GAGCACCCAACAGAAGCAATTG GAGAGTTTGG-
TAAATCTACTGACGCAGGGAAGCAGGT-
TCTACCGCAAAG
CATATAATGAACTGTTCTCAGGTGTAAC-
TACTGAGCAGGATCCGGATTCA TCGACTAATAT-
TCCTGAGTATATGCTTTTGGGTG-
GCATCTCTTCTTAATG
CTCCATTTGAGATCACCAGAATTGT-
TCAAGGACCTGGTGTCCTGCATCCA TGGATT-
AGTTGCTGTGTTGGCCATACTTTTGAT-
TCACGTGCCAGCTAAATT
TAGGAGCTTCACGATTGAAGGCTCTTCT-
CACTTAATCAAACAAACTGAGA AAGGCGTG-
GATCTTATTGCTTCATTATGTCATAAC-
TATCATACCTCTGAA
GAACGTTTGAAAGAAATGTTGCA-
CAAGTCTCACAATGCAATAGAAGACA TTTTC-
CATATGAAAGCACTAAGTGCTTCAGAGT-
GCAAACCAGAQAAATTTG
GATAAGATAGACACAGATGACCTGATG-
TATTTCAAGGTCTGATTGATAT GGAATGTTTC-
CAGTCAAATTTGGAAAAAATGGAGAAAC-
TATGTAATTCTA
ATAGCTGTAAAGGGGAGCTTGATTT-
TAAATCAATTTTGATCAATAATGAT TATATTC-
CCTATGATGAGAACTCGACGGGGGATTC-
CACCAATTTAGGACA
TTCAAAGTGTGCCTTTGAAACATTG-
GCATCTCCCACAAAGACAATAAAGA ACATGCT-
GACTGTTCCTAGTTCTCCTTTGTCAC-
CAGCCACCGGTGGTTCAG
TCAAGATTGTGCAAATGACACCAG-
TAACTTCTGCCATGACGACAGCTAA GTGGCT-
TCGTGAGGTGATATCTTCATTGCCA-
GATAAGCCTTCATCTAAGC
TTCAGCAGTTTCTGTCATCATGCGAT-
AGGGATTTGACAAATGCTGTCACA GAAAGGGT-
CAGCATAGTTTTGGAAGCAATTTTTC-
CAACCAAATCTTCTGC
CAATCGGGGTGTATCGTTAGGTCTCAAT-
TGTGCAAATGCCTTTGACATTC CGTGGGCA-
GAAGCCAGAAAAGTGGAGGCTTCCAAGT-
TGTACTATAGGGT
ATTAGAGGCAATCTGCAGAGCGGAGTTA-
CAAAACAGCAATGTAAATAAT CTAACTCCAT-
TGCTGTCAAATGAGCGTTTCCACCGAT-
GTTTGATTGCATGT
TCAGCGGACTTAGTATTGGCGACACAT-
AAGACAGTCATCATGATGTTTCC TGCTGTTCT-
TGAGAGTACCGGTCTAACTG-
CATTTGATTTGAGCAAAATAA
TTGAGAACTTTGTGAGACATGAAGAGAC-
CCTCCCAAGAGAATTGAAAAG GCACCTAAATTC-
CTTAGAAGAACAGCTTTTGGAAAGCATG-
GCATGGGAG
AAAGGTTCATCATTGTATAACTCACT-
GATTGTTGCCAGGCCATCTGTTGC TTCA-
GAAATAAACCGCCTTGGTCTTTTGGCT-
GAACCAATGCCATCTCTTG
ATGACTTAGTGTCAAGGCAGAATGTTCG-
TATCGAGGGCTTGCCTGCTACA
CCATCTAAAAAACGTGCTGCTGGTCCA-
GATGACAACGCTGATCCTCGATC ACCAAA-
GAGATCGTGCAATGAATCTAGGAACA-
CAGTAGTAGAGCGCAAT
TTGCAGACACCTCCACCCAAGCAAAGC-
CACATGGTGTCAACTAGTTTGAA AGCAAAATGC-
CATCCACTCCAGTCCACATTTGCAAGTC-
CAACTGTCTGTA
ATCCTGTTGGTGGGAATGAAAAATGT-
GCTGACGTGACAATTCATATATTC TTTTCCAA-
GATTCTGAAGTTGGCTGCTATTA-
GAATAAGAAACTTGTGCGA
AAGGGTTCAATGTGTGGAACAGACA-
GAGCGTGTCTATAATGTCTTCAAG CAGATTCT-
TGAGCAACAGACAACATTATTTTT-
TAATAGACACATCGATCA
ACTTATCCTTTGCTGTCTTTATGGTGT-
TGCAAAGGTTTGTCAATTAGAACT CACAT-
TCAGGGAGATACTCAACAATTACAAAA-
GAGAAGCACAATGCAAG
CCAGAAGTTTTTTCAAGTATCTATAT-
TGGGAGTACGAACCGTAATGGGGT ATTAG-
TATCGCGCCATGTTGGTATCAT-
TACTTTTTACAATGAGGTATTTGT
TCCAGCAGCGAAGCCTTTCCTGGTGT-
CACTAATATCATCTGGTACTCATC CAGAAGA-
CAAGAAGAATGCTAGTGGCCAAATTC-
CTGGATCACCCAAGCC
ATCTCCTTTCCCAAATTTACCAGATAT-
GTCCCCGAAGAAAGTTTCAGCAT CTCATAATG-

TATATGTGTCTCCTTTGCGGCAAACCAAGTTGGATCTACTG
CTGTCACCAAGTTCCAGGAGTTTTTATGCATGCATTGGTGAAGGCACCCA TGCTTATCAGAGCCCATCTAAGGATTTGGCTGCTATAAATAGCCGCCTAA
ATTATAATGGCAGGAAAGTAAACAGTCGATTAAATTTCGACATGGTGAG TGACTCAGTGGTAGCCGGCAGTCTGGGCCAGATAAATGGTGGTTCTACCT
CGGATCCTGCAGCTGCATTTAGCCCCCTTTCAAAGAAGAGAGACAGA TACTTGATCAATTATAAATGGTGGCCTCTCTCGTATATAGCTCACAGATC
CGTGCTCCGTAGCAGTCTATTCTTCTGAATAAGTGGATTAACTGGAGCGA TTTAACTGTACATGTATGTGTTAGTGAGAAGCAGCAGTTTTAGGCAGCA
AACTGTTTCAAGTTAGCTTTTGAGCTATCACCATTTCTCTGCTGATTGAAC ATATCCGCTGTGTAGAGTGCTAATGAATCTTTAGTTTTCATTGGGCTGAC
ATAACAAATCTTTATCCTAGTTGGCTGGTTGTTGGGAGGCATTCATCAGG GTTATATTTGGTTGTCAAAAGTACTGTACTTAATTCACATCTTTCACATT
TTTCACTAGCAATAGCAGCCCCAAATTGCTTTCCTGACTAGGAACATATT CTTTACAGGTATAAGCATGCCAACTCTAAACTATATGAATCCTTTTATAT
TCTCATTTTAAGTACTTCTCTGTTTCTGCTACTTTTGTACTGTATATTTCC AGCTTCTCCATCAGACTGATGATCCCATATTCAGTGTGCTGCAAGTGATT
TGACATATGTGGCTTATCCTTCAGGTATGTCTCATGTTGTGACTTCATTGC TGATTGCTTTTGTAATGGTACTGTTGAGTTCATTTCTGGTTACAATCAGCC
TTTACTGCTTTATATTGTTCTACTAATTTTGGCTTGCACAGCCAGGACGAT TGGTTTTCTGCATCAATCAATCTTTTTTAGGACAAGATATTTTTGTATGCT ACACTTCCCAAATTGCAATTAATCCAGAAGTCTACCTTGTTTTATTCTATT
AGTTCTCAGCAACAGTGAATGAATATGAATCAGTCATGCTGATAGATGTT CATCTGGTTATTCCAAACAATCTGACATCGCATCTCTTTCTGCAAGTGAG
ATGAAGAAAACCTGAAATGCTATCACCATTTAAAACATTGGCTTCTGAAG TTCAGGTGATTAGCAGGAGACGTTCTGACATTGCCATTGACATGTACGGT
AGTGATGGCAGGAGACGTTCTTAAACAGCAGCTGCTCCTTCAGCTTGTAA TGTCTGATTGTATTGACCAAGAGCATCCACCTTGCCTTATGGTACTAACT
GAATGAGCTGGTGACGCTGACTCATCTGCATAATGGCAGATGCTTAACCA TCTTTAGGAGCTCATGTCATGATTCCAGCTGCACCGTGTGCAAATGTGAA
GGCCCTGCAAGGGCTTTCCAGGCCGCACCAATCCTGCTTGCTTCTTGAAG ATACATATGGTGCCACCTAAATAAAAGCTGTTTCTGGTTATGTCTGTCCTT
GACATGTCAACAGATTAGTGTTGGGTTGCAGTCGTGTGGTGTTTAAGTCT TGGAGAAGGCGAGAAGTCATTGCTGCCAGCATTGT GTCGTCAGGCACAG
AAGTACTCAAAAGTGAGAGCTACTTTGTTGCGAGCAAACGGAGGGCGAT ATAGGTTGATAGCCAATTTCAGTTCTCTATATACAAGCAGCGGATTTTGT
TTAGAGTTAGCTTTTGAGATGCATCATTTCTTTCACATCTGATTCTGTGTG TTGTAACTCGGAGTCGCGTAGAAGTTAGAATGCTAACTGACCCTTAATTT
TCACCGAATAATTTGCTAGCGTTTTTCAGTATGAAAAAAAAAAAAAAAAAAAAAAAAAAAAA

SEQ ID NO:4—*Zea mays* RRB1 Polypeptide Sequence

MSSLDPSPATSTQQKQLESLVNLLTQGSRFYRKAYNELFSGVTTEQDPDSST NIPEYMLFGWHLFLMLHLRSPELFKDLVSCIHGLVAVLAILLIHVPAKFRSFTI
EGSSHLIKQTEKGVDLIASLCHNYHTSEERLKEMLHKSHNAIEDIFHMKALS ASECKPENLDKIDTDDLMYFKGLIDMECFQSNLEKMEKLCNSNSCKGELDF
KSILINNDYIPYDENSTGDSTNLGHSKCAFETLASPTKTIKNMLTVPSSPLSPA TGGSVKIVQMTPVTSAMTTAKWLREVISSLPDKPSSKLQQFLSSCDRDLTNA
VTERVSIVLEAIFPTKSSANRGVSLGLNCANAFDIPWAEARKVEASKLYYRV LEAICRAELQNSNVNNLTPLLSNERFHRCLIACSADLVLATHKTVIMMFPAV
LESTGLTAFDLSKIIENFVRHEETLPRELKRHLNSLEEQLLESMAWEKGSSLY NSLIVARPSVASEINRLGLLAEPMPSLDDLVSRQNVRIEGLPATPSKKRAAGP
DDNADPRSPKRSCNESRNTVVERNLQTPPPKQSHMVSTSLKAKCHPLQSTFA SPTVCNPVGGNEKCADVTIHIFFSKILKLAAIRIRNLCERVQCVEQTERVYNV
FKQILEQQTTLFFNRHIDQLILCCLYGVAKVCQLELTFREILNNYKREAQCKP EVFSSIYIGSTNRNGVLVSRHVGIITFYNEVFVPAAKPFLVSLISSGTHPEDKK
NASGQIPGSPKPSPFPNLPDMSPKKVSASHNVYVSPLRQTKLDLLLSPSSRSF YACIGEGTHAYQSPSKDLAAINSRLNYNGRKVNSRLNFDMVSDSVVAGSLG QINGGSTSDPAAAFS PLSKKRETDT

SEQ ID NO:5—*Zea mays* RRB2a cDNA Sequence

GAGAATTGAAAAGACACCTAAATTCCTTAGAAGAACAAATTTTGGAAAG CATGGCATGGGAGAAAGGTTCATCATTGTATAACTCACTGATTGTTGCCA
GGCCATCTGTTGCTTCAGAAATTAATCGCTTTGGTCTTCTGGCTGAATCA ATGCCATCTCTTGATGACTTAGTGGCAAGGCAGAATATTCATATTGAGGG
CTTGCCTGCTACACCATCTAAAAAACGTGCTGCTGGTCGAGACGACAATG CTGATCCTCGATCACCAAAGAGACCATGCAATGAATCTAGGAGCACAGT
AGTAGAACACAATTTGCAGACACCTCCACCCAAGCAATGCCACATGGTG TTGACTAGTTTGAAAGCAAAATGCCATCCACTCCAGTCCACATTTGCAAG
TCCAACTGTCAGTAATCCTGTTGGTGG

GAACGAAAAATGTGCTGACGTGA CAATTCAGATATTCTTTTCCAAAATTCTGAAGTTAGCTGCTATTAGAATA
AGAAACTTGTGTGAAAGGATTCAATATATGGAACAGACAGAGCGTGTCT ATAATGTCTTCAAGCAGATTCTTGATCAACAGACAACATTATTTTTAAT
AGACACATGCATCAACTTATTCTTTGCTGTCTTTATGGTGTTGCAAAGGTT TGCCAATTAGAACTCTCATTCAGGGAGATACTCAACAATTACAAAAAG
AAGCACAATGCAAACCAGAAGTTTTTTAAGCATCTATATTGGAAGTAGG AATCATAATGGGGTATTAATATCACGCCATGTTGATATCATTACTTTTTAC
AATGAGGTCTTTGTTCCAGCAGCCAAGCCTTTCCTGGTGTCATTAATATC ATCTGGTACTCGTCCAGAAGACAAGAAGAATGCTAGTGGCCAAGTTCCT
GGATCACCGAAGCTATCTCCTTTCCCAAATTTACCAGATATGTCCCCAAA GAAAGTTTCAGCTTCTCATAATGTATATGTGTCTCCTTTGCGGCAAACCA AGATGGATTTACTGCTGTCACCAAGTTCCAGGAGTTTTTATGCATGCATT
GGTGAAGGCACCCATGCTTATCAGCCCATCTAAAGATTTGGCTGCTAT AAATAGCCGCCTAAATTATAATGGTCGGAGAGTAAACAGTCGATTAAAC
TTTGACATGGTGAGCGACTCAGTGGTAGCTGGTAGTCTAGGCCAGCCAA ATGGTGGTCTACTTCCTTGGATCCTGCAGCTGCATTTAGCCCCCTTTCAA
AGAGAAAGCCAGATACTTGATCAAATATAAATGGCGATCTCTCTCGTATA TAGCTCACAGCTCCATAGCAGTCTATTCTTCTGAATAAGTGGGTTGACTG
GAGTGATTTAACTGTACATGTATGTGTTAGTGAGAACCAGCAGTTTATAG GCAGCAAACTGTTTTAAATTAGCTTTGAGGTTTTATCACCATTTCCCTGCT
GATTGAACATATTTTAGATTGTAACATCTGCTTTGTAGAATGCTAATGAA TCTTTAGTTTTCAGTGGGTTGACATTAAAAATCCTTATCCTAGTTGGCTGG
TTGTTGGGAGACATTCATCAAGGTTATATTTGGTCGTCAAATAGTACTGT ACTTGATTCATATCTTTCATATTTTTCACTAGCGTTGGCAACCGTAAATTG
CTTTCCTGACTAGGAACATATTCTTCACAAGTATGGCAACTCTAAACTAT TTGACCTTTTATATTCTCATTTTTAAGTACTTTCTCTATTTCTGCTACTTTT
GTACTGTGTATTTCCAGCTTCTCCACCAGACTGATTGTTAGAGTGTATGCT CCTATATTATCCATGTATGTGTAAATGGGCTGCTAGCCCATTAGGGTTAG
GTTCCCCTGGGTCTATATATGTAACCACCCTCTATGCAATAGAAGTTGAA TATCAGTTTCTATCACTAATGATTCCATATTCAGTGGGCTGCAAGTGATTT
GACATACGTGCCTTATCCTTCAGGTATGTCTCATGTTGACTTTGCTTTTGT AATGGTACTGTTGGCTTCATTGCTGGAATGCTGGTTATAATCAACCTTTA
CTGCTCTATATTGTTCTTTTTTGGTTTGCACAACCAGGGTGGTTGGTTTT CTGAAT

CAATCAATCCATTTCCTCGGACGACAAGATAATTTTTGTATGTT
ACACTTCCCAAAATTGCAATTAATTCAGAAGTCTGCCTACTTTCATTCAG TTAGTTCTCAGCAACACTGAAAGGATATGAATCAGTCAACCCGATAGAT
GTTTATCTGGTTATTCCAAACAATCTGACATCACATCTGTTTCTGCAGGCG AGATAAGGAAAATCTGAAATGCTATCACCATTTAAAACATTGGCTCCTGG
AAGTTCAGGTAGGTGTTGCTGTAGAATGAGATGGTTAGGAATCTTTACAA GCTCAGGCTATATGATTTCAGCAGCACTGTAACCTGGGGTGCAAATGTTA
AGGCCCTGCAAGCACTTTCCAGGCCACACCAATTCTGCTTGGTTCTTGAA GATACATTCTTCCTATGTGCCCCCTATATAAAAGCCATTTCTGGTTGTTAT
GTTTATCCTTGACATGTCAACAGATTAGTGTTGGGTTGCAGTCATGCGGT CCTTAAGTCTCGGAGAAGGCGAGAAGTCATTGCTGCTAGCATTGTGATCG
TCGGCCACGAAAGTAATCAAAAGTGAGAGCTACTTGTTCCTAGCAAAT GGAGAAGGGCGATATATAGGTTTATGATCAAATTCAGTGTATGCAAGCA GCATATTTTGTTTAGAGTTAGCTTTTGAGGTTCATCATTTCATTTCACAGC
TGATTCTCTATGTTGTAACTCCTTAGTCGTGTAGAAATTAGAATGCTATCT GCTTAATTTTTAGTGAATAATTTGCTAGTATATTTTTGAATGTAATTGCAG
TAGCTCTGCCTCTTCATTAAGGAAAAAAAAAAAAAAAAA

SEQ ID NO:6—*Zea mays* RRB2a Polypeptide Sequence

ELKRHLNSLEEQILESMAWEKGSSLYNSLIVARPSVASEINRGLLAESMPSL DDLVARQNIHIEGLPATPSKKRAAGRDDNADPRSPKRPCNESRSTVVEHNLQ
TPPPKQCHMVLTSLKAKCHPLQSTFASPTVSNPYGGNEKCADVTIQIFFSKIL KLAAIRIRNLCERIQYMEQTERVYNVFKQILDQQTTLFFNRHMHQLILCCLY
GVAKVCQLELSFREILNNYKKEAQCKPEVFLSIYIGSRNHNGVLISRHVDIITF YNEVFVPAAKPFLVSLISSGTRPEDKKNASGQVPGSPKLSPFPNLPDMSPKKV
SASHNWYVSPLRQTKMDLLLSPSSRSFYACIGEGTHAYQSPSKDLAAINSRLN YNGRRVNSRLNFDMVSDSVVAGSLGQPNGGSTSLDPAAAFSPLSKRKPDT

SEQ ID NO:7—*Zea mays* RRB2b cDNA Sequence

CCTAGTTCCCCTTTGTCACCCACCAACGGTGGTTCAGTCAAGATTGTGCA AATGACACCAATAACTTCTGCCATGACGACAGCTAAGTGGCTTCGTGAG
GTGATATCTTCATTGCCAGAGAAGCCTTCATCTAAGCTTCAGCAGTTGAT GTCATCATGCGATAGAGATTTGACAAATGCCGTCACAGAAAGGGTCAGC
ATAGTTCTGGAAGCAATTTTTCCAACCAAGTCTTCTGCTGATCGGGGTGG CTCATTAGCCTCAATTGTGCAAATGCCTTTGATACTCTATGGGCAGATG

CCAGAAAAATGGAGGCTTCCAAGTTG-
TACTATAGGGTATTAGAGGCAAT CTGCAGAGCT-
GAGTTACAAAACAGCAATGTAAA-
CAATCTAACTCCATTG
CTGTCAAATGAGCGTTTTCACCGAT-
GTTTGATTGCATGTTCAGCGGAGCT AGTATTGGC-
GACACATAAGACGGTCATCATGAT-
GTTTCCTGCTGTTCTTG
AGAGTACTGGTCTAACCT-
CATTTGATTGAGCAAAATAATTGAGAACTTT
GTGAGACATGAAGAGACCCTCCCAA-
GAGAATTGAAAAGACACCTAAATT CCTTAGAA-
GAACAAATTTTGGAAAGCATGGCATGG-
GAGAAAGGTTCATC
ATTGTATAACTCACTGATTGTTGCCAG-
GCCATCTGTTGCTTCAGAAATTA ATCGCTTTG-
GTCTTCTGGCTGAATCAATGCCATCTCT-
TGATGACTTAGTGG
CAAGGCAGAATATTCATATTGAGGGCT-
TGCCTGCTACACCATCTAAAAAA CGTGCTGCTG-
GTCGAGACGACAATGCTGATCCTCGAT-
CACCAAAGAGAC
CATGCAATGAATCTAGGAGCACAGTAG-
TAGAACACAATTTGCAGACACC TCCACCCAAG-
CAATGCCACATGGTGTTGAC-
TAGTTTGAAAGCAAAATGCC
ATCCACTCCAGTCCACATTTGCAAGTC-
CAACTGTCAGTAATCCTGTTGGT GGGAAC-
GAAAAATGTGCTGACGTGACAATTCA-
GATATTCTTTCCAAAAT
TCTGAAGTTAGCTGCTATTAGAATAA-
GAAACTTGTGTGAAAGGATTCAAT ATATGGAA-
CAGACAGAGCGTGTCTATAATGTCT-
TCAAGCAGATTCTTGAT
CAACAGACAACATTATTTTTAATAGA-
CACATGCATCAACTTATTCTTTG CTGTCTTTATG-
GTGTTGCAAAGGTTTGCCAATTA-
GAACTCTCATTCAGGG
AGATACTCAACAATTACAAAAAAGAAG-
CACAATGCAAACCAGAAGITTT TTTAAGCATC-
TATATTGGAAGTAGGAATCATAATGGGG-
TATTAATATCAC
GCCATGTTGATATCATTACTTTTTA-
CAATGAGGTCTTTGTTCCAGCAGCCA AGC-
CTTTCCTGGTGTCATTAATATCATCTGG-
TACTCGTCCAGAAGACAAG
AAGAATGCTAGTGGCCAAGTTCCTGGAT-
CACCGAAGCTATCTCCTTTCCC AAATTACCA-
GATATGTCCCCAAAGAAAGTTTCAGCT-
TCTCATAATGTAT
ATGTGTCTCCTTTGCGGCAAACCAA-
GATGGATTTACTGCTGTCACCAAGT TCCAG-
GAGTTTTTATGCATGCATTGGTGAAG-
GCACCCATGCTTATCAGAG
CCCATCTAAAGATTTGGCTGCTATAAAT-
AGCCGCCTAAATTATAATGGTC GGAGAGTAAA-
CAGTCGATTAAACTTTGACATGGTAT-
GTCTCATGTTGACT
TTGCTTTTGTAATGGTACTGTTGGCT-
TCATTGCTGGAATGCTGGTTATAAT CAACCTT-
TACTGCTCTATATTGTTCTTTTTTG-
GTTTGCACAACCAGGGTG
GTTGGTTTTCTGAATCAATCAATC-
CATTTCCTCGGACACAAGATAATTTTT
GCGAGATAAGGAAAATCTGAAATGCTAT-
CACCATTTAAAACATTGGCTC CTGGAAGTTCAG-
GTTAGGTGTTGCTGTAGAATGAGATGGT-
TACCATCTTT
ACAAGCTCAGGCTATATGATTTCAGCAG-
CACTGTAACCTGGGGTGCAAAT GTTAAGGCCCT-
GCAAGCACTTTCCAGGCCACACCAAT-
TCTGCTTGGTTCT
TGAAGATACATTCTTCCTATGTGC-
CCCCTATATAAAAGCCATTTCTGGTTG TTATGTT-
TATCCTTGACATGTCAACAGATTAGTGT-
TGGGTTGCAGTCATGC
GGTCCTTAAGTCTCGGAGAAGGC-
GAGAAGTCATTGCTGCTAGCATTGTGA TCGTCG-
GCCACGAAAGTAATCAAAAAGTGAGAGC-
TACTTGTTCCTAGCA
AATGGAGAAGGGCGATATATAGGTTTAT-
GATCAAATTCAGTGTATGCAA GCAG-
CATATTTTGTTTAGAGTTAGCTTTTGAG-
GTTCATCATTTCATTTCAC
AGCTGATTCTCTATGTTGTAACTCCT-
TAGTCGTGTAGAAATTAGAATGCT ATCTGCT-
TAATTTTTAGTGAATAATTTGCTAG-
TATATTTTTGAATGTAATT
GCAGTAGCTCTGCCTCTTCAT-
TAAAAAAAAAAAAAAAAAAA

SEQ ID NO:8—*Zea mays* RRB2b Protein Sequence

PSSPLSPTNGGSVKIVQMTPITSAMT-
TAKWLREVISSLPEKPSSKLQQLMSSC DRDLT-
NAVTERVSIVLEAIF-
PTKSSADRGGSLGLNCANAFDTLWADARKME
ASKLYYRVLEAICRAELQNSNVNNLT-
PLLSNERFHRCLIACSAELVLATHKT VIMMFPAV-
LESTGLTSFDLSKIIENFVRHEETL-
PRELKRHLNSLEEQILESMA
WEKGSSLYNSLIVARPSVASEINRF-
GLLAESMPSLDDLVARQNIHIEGLPATPS
KKRAAGRDDNADPRSPKRPC-
NESRSTVVEHNLQTPPPKQCHMVLTSLKAKC
HPLQSTFASPTVSNPVGGNEKCADVTI-
QIFFSKILKLAAIRIRNLCERIQYMEQ TERVYNVFK-
QILDQQTTLFFNRIfMHQLILCCLYG-
VAKVCQLELSFREILNNY
KKEAQCKPEVFLSIYIGSRNHNGVLIS-
RHVDIITFYNEVFVPAAKPFLVSLISSG TRPEDKK-
NASGQVPGSPKLSPFPNLPDMSP-
KKVSASHNVYVSPLRQTKMDL
LLSPSSRSFYACIGEGTHAYQSPSKD-
LAAINSRLNYNGRR VNSRLNFDMVCLMLTLLL

SEQ ID NO:9—Arabidopsis RRB Genomic
Nucleotide Sequence

Nucleotides
 1–543 5' untranscribed
 544–653 5' untranslated (start of cDNA)
 654–1093 intron 1
 1094–1107 5' untranslated
 1108–1189 start codon/exon 1
 1190–1307 intron 2
 1308–1410 exon 2
 1411–1497 intron 3
 1498–1641 exon 3
 1642–1721 intron 4
 1722–1817 exon 4
 1818–1902 intron 5
 1903–1951 exon 5
 1952–2216 intron 6

2217–2409 exon 6
2410–2540 intron 7
2541–2606 exon 7
2607–2693 intron 8
2694–2873 exon 8
2874–2973 intron 9
2974–4029 exon 9
4030–4124 intron 10
4125–4287 exon 10
4288–4385 intron 11
4386–4458 exon 11
4459–4579 intron 12
4580–4756 exon 12
4757–4869 intron 13
4870–4969 exon 13
4970–5051 intron 14
5052–5184 exon 14
5185–5276 intron 15
5277–5390 exon 15
5391–5497 intron 16
5498–5613 exon 16
5614–5695 intron 17
5696–5870 exon 17/stop codon
5871–6081 3' untranslated
6082–6421 3' untranscribed GATCCTACTCACACTCGAAGATGACGAA-
GAAGACTTAATCTGAATCCATC CGCGGATAGGA-
CACTCATACTTCTGCAACCAAACGTTC-
TACAATGGCAA
ATATGTAATTTCCCGCGTGACCTAAAC-
TAGAAACGGCATCGTATTAAGGG TGGGCCCAAT-
CATAACTCACACGAGGCTTTGTCGCGGT-
CACGAAAACCC
AGACGGCGTTAATGGCCCACTC-
CGTTTGTTTCGACCCCGCCGTGACGGCG
AATCTTTCCCTCTCAGCGTTTCACGCAA-
CAGTAAGTAAGTTTTGGCGGTA AAATTGGGTCA-
CAGATGGGTACGTGTCGATTTAATAGTG-
GTTGAAAGCG
CGCGAATATAATTGTATACGTATGTG-
TATGTATTCTCCGTGTTGTTTTTCC CGCGC-
GAGATATATCCTTTTTTAGGGGTTTGCCG-
CATAATCAGACCCCATT
CTAGAGAGAAGAGGGAAGTCAGGT-
GAAGATAGAGAGAGACACTGAG AGGAGG-
GAAAATTTGTAGGGTTTCCG-
GAGATCTCTGTGATTCCTCTGAAT
TTGTCGAATTTTTTGGAGGAGGCGTTA-
GAAGTCGGGCTTCTTAAAAATCA GATCTTCT-
GCTCAGCTTTAATCGGCGACGTCTGG-
TATTGGGATCTGTGAC
ACAAAAGGTAAGATCTTTCTCTATTGC-
CTATCCTTTGATTTGAAATCTTA TCCTCTAGGTG-
GTTTATCTGAAATTTCTAT-
TGATATTTCGCTATTCGATT
GTAAGTTGGTGAGAGAATTCTCCAAAAA-
CAAAAAAGAGAAAAACTTTGA ATGAATATTTAA-
GATAACATCTGGGTAAAATTTTCCG-
GAGTGGTGGGTT
TTAGATTATGCCCCAATTTCTCT-
TCTTTTTTTCCCCCAAATTTTGTCTTTCT GCCAT-
GTTTTGGGAAATTGGGAGTTTGTTTTCT-
CATGTCTGTTAGTGTGTT
CTTCCGAATGGGTTGGGCATGGTTC-
CTATTGAATTTCAGTGTGATTAAAT TAA-
CAAATCTCTTTGCTTGAAAAGTC-
CCTTTTTCTTCGTCTTCAGTTAGCA
GTTTAATTGGAAGTAAAATTAGCT-
TGATTTGCATGTTTTCAGCTGCGTTG GAGAC-
TATGGAAGAAGTTCAGCCTCCAGTGAC-
CCCGCCCATTGAACCAA
ATGGGAAAAGAAGCGAAGCCTCTCTCT-
TGGACATATGCGAGGTTTACTCT TCTCTTTGCT-
GATCTAGTTGCATTTGTTTAGTTGAA-
GATACCATTTGAGTT
CTCTCGGAAATTTTGAGGAC-
TAGCTCTAATCCCTGTAGTTGATTTCTTATT GCA-
GAAAGTTCTGTCTCTTGATGGGAGCACT-
TGCGATGAAGCTTTGAAGT
TGTTTACAGAAACCAAACGAATTTTGT-
CAGCAAGCATGTCTAACATTGGA AGTGGAACG-
GTGAAATACATTTTTCCTCTAACT-
TCTCTTTTATCAGTTAAC
TGTGGTTTCATTATGACTAAATC-
CTTTTTTCTTCTTCTTATTAGCGGGAAG AAGTA-
GAGAGGTTCTGGTTTGCGTTTATTCTC-
TATTCAGTGAAGAGGCTT
AGTGTGAGAAAAGAAGCGGATGGTCTGT-
CAGTGTCTGGTGATAATGAGT TTAATCTATGTCA-
GATACTGAGGGCTCTGAAGCTAAAG-
TAAGTAGTGTTC
AATTCTTCCTTCCTTGTCATTCTTAAAT-
TCATTTGTAGTGACGATTTTCCTC TTTTCTGTT-
TATAGTATTGTGGATTTTTTTAAAGAGT-
TACCTCAGTTTGTG
GTCAAGGCTGGATCTGTACTGGGT-
GAACTTTACGGCGCAGACTGGGAGA ACAGACT-
TCAGGTTTTGACTAACATCTTT-
TAAATATACTTCTACTTCTATT
ATATCATTGTTAAATATGCTTCTAT-
TAACTAATTTTTACTTACTAGGCAAA GGAGGTG-
CAGGCTAACTTTGTGCATCTTAGCCT-
TCTAAGCAAGTGAGTTT
AGCTCCCTTCCTATTTTACATT-
TATCTTTGTTTTGTGTAAGAATAGTTATT GACATA-
GATTTCATATTTTGGACCTGCAACTTA-
GAAGCAAATTTTCTTCCT
ATGCAATAATCAGAATATGGGCTTG-
CAATATTCCTTCCATTTAAATTAA TTAAGATTTA-
GAGTTACAGATTTCTGGTTTTCATGT-
GATTATATTCTGTGA
ATTGTTTAAGGACATGTTAAAGTAT-
GATGTTTTGGTACCTTTCCTTGGT AACAGATAC-
TACAAACGTGGGTTCCGGGAAT-
TCTTTTTGACATATGATGC
AAACGCAGAAAAGAACTCAGCAAACTCT-
TCTACCTATTTGCTGGATAGTT ATCGTTTTGGATG-
GCTACTCTTTTGGCACTCCGAAACCAT-
GCGTTAGTC
GATTTAAGGACCTCGTGACATGCT-
CAAATGGCGTAGTTCTATATTGGTT AGTGAC-
TACCTGTGGAGCTCTC-
CCTAATCTTTCATTCATTTAGTCTTGCT
GTACATTATTACTTGAAAGATGCT-
TCGTTTAATATAACGCAATTGAAGTA TAG-
GCTAACTCCTTTTCATGTTATCAGGC-
TATTTTGATCATACATGTTCCT
TGTCGGTTTAGAAATTTCAGCATCCAA-
GATTCTTCTCGCTTTGGTGAGTGT TTATCTTTTCT-
TCTATCCCGATAACCATGGCACCATA- GAATGTTTATCATC
TATTTTCATTTATGTGATGAATCTCAGT-
TAAGAAAGGTGACAAAGGTGTA GACTTGGTTG-
CATCACTTTGCAAGATATATGACGCCT-
CAGAAGATGAGTT
GAGGATAGTAATTGACAAG-
GCAAATAATTGGTAGAAACCATACTGAAG
AAAAAGCCATCTCCAGCATCTGAGTGC-
CAAACTGACAAGCTAGATAATA TTGACCCAGGT-
TGGTCTAAAATCATTTTCCTTCTTCAAT-
TAAAGAATCATG
TGAGTTCATTGAACAGTTGCCTGATTGT-
TCTTCGAATCTATATGGTGTTTT ACTGCAGATG-
GCTTGACCTACTTTGAGGATTTACTG-
AAGAGACGTCCAT
CTCAACTAGCTTAATTACACTTGAAAAG-
GATTACTATGATGGTAAAGGCG AACTTGAT-
GAGAGGGTATTCATCAATGAAGAGGAT-
AGCTTACTTGGATCT
GGAAGCTTATCTGCAGGAGCTGT-
TAATATTACTGGTGTTAAGAGGAAAAT TGAT-
GCTTTGAGCTCACCTGCAAGGACATT-
TATAAGCCCACTTTCTCCTC
ATAAGTCGCCTGCTGCTAAGACAAATGG-
TATTAGCGGTGCTACCAAGTTG GCAGCAACAC-
CAGTGAGCACAGCAATGACAACTGC-
CAAGTGGCTCAGGA
CTGTCATATCCCCGCTTCTGCCAAAAC-
CTTCTCCTGGGTTGGAACATTTCC TTAAATCAT-
GTGATAGGGATATAACAAATGACGTCA-
CACGAAGAGCACA
CATAATATTGGAAGCTATTTTCCCAAAT-
AGTTCCCTTGGTGCCCAATGTG GAGGTG-
GAAGTTTGCAAGCTGTTGACCTGATG-
GATGACATATGGGCAGA
GCAGCGCAGATTAGAAGCTTGTAAGT-
TATACTACAGAGTTCTTGAGGCA ATGTGTAAAG-
CAGAAGCTCAGATTTTGCATG-
CAAATAATCTGAACTCTTT
ATTGACAAATGAGAGGTTCCATAGATG-
CATGCTTGCTTGCTCAGCTGAAT TGGTACTGGC-
TACCCACAAAACAATTACAATGTTGTTC-
CCAGCTGTTCTG
GAGAGGACTGGGATCACAGC-
CTTTGATCTCAGCAAGGTAATTGAGAGTT TCAT-
ACGACATGAAGATTCTCTGCCTA-
GAGAGTTGAGACGACATCTGAAT
TCACTGGAGGAACGGCTTCTAGAGAG-
TATGGTATGGGAGAAAGGCTCTT CAATGTACAAT-
TCTCTGATTGTTGCCAGGCCATCGCTTG-
CATTGGAGATA
AATCAGCTCGGTTTACTAGCTGAAC-
CAATGCCATCTCTGGATGCAATCGC AGCACTTAT-
TAATTTCTCTGACGGAGCAAATCATG-
CATCATCTGTACAAA
AGCATGAAACTTGTCCAGGTAGTTT-
TATTTGTTTCTGAATTAAAGCAGTTT TCCAACCT-
GCTGTTAATGGTATGATTTTCTTAC-
CAAAAATTGTCAAATTTG
CTGCCATATAGGACAAAATGGGG-
GATTAGATCGCCCAAAAGATTATGT ACTGATTAC-
CGCAGCATTCTAGTTGAACGCAATTC-
CTTTACATCACCAGT
AAAGGATCGTCTGTTGGCCTTAG-
GCAACGTTAAATCCAAGATGCTGCCAC CTCCGT-
TGCAGTCTGCATTTGCCAGGTA-
CATTTTGAGTAACTATGAGTAG
AAATGGAGAGTTAGTTTACCTATCTAGT-
TGTCCCTGTACTTGTTAAGTAA CCTCTTCGGATT-
TATGTCTACAGCCCAACACGGCCCAAC-
CCAGGAGGTGG
AGGAGAAACTTGTGCAGAAACTGGAAT-
CAATATTTTCTTCACAAAGGTA GGTCTGT-
GAGATCTTTGGATCTACTAC-
TAATCGTTTGGTTAGATGATGTA
CTACAAAACACGGTATTGATTCT-
TCATTTTCGGCTGGGAATTGTGTTAAATGTGGTG-
GCTCTTCCCAGATTAATAAATTGGCT-
GCTGTAAGAATCAATGG
AATGGTGGAAAGACTACAACTTTCACAG-
CAAATAAGGGAGAGTGTGTAT TGTTTCTTCCAA-
CATGTACTTGCTCAGCGGACTTCTCTTT-
TATTCAGTCGA
CACATTGACCAGATCATTCTCTGTTGCT-
TCTACGGAGTGGCCAAGGTGAG TAGTGTGAT-
TCAAAGGGTTTAACTATATGTCATCTG-
GTTTACAATGGCTT
CTCTTACACTTACACTTTTTCCATGAAT-
CACCTTGTAGATATCCCAAATGA GCCT-
GACTTTCAGGGAAATCATATACAACTAC-
CGGAAGCAACCACAGTG
TAAACCATTAGTTTTCCGCAGCGTTTAT-
GTGGATGCGTTACAATGTCGCC GTCAAGGGG-
TATATATACACTCTTAACCTTATGCT-
GAAAAGTTTCTTTAC
TCGGTGGAGAAGACTAAATTTGTGA-
CAATGACTTGAACAGAGAATAGGG CCAGATCAT-
GTTGACATCATCACATTCTACAAT-
GAAATATTTATTCCTGC
CGTAAAGCCGCTGCTGGTGGAGCTAG-
GTCCTGTAAGAAACGACCGGGCT GTGGAAGC-
CAATAATAAGCCTGAAGGTAGTTAA-
GAAAGGCCAGATACTT
GTTAGATGTAAGCTTTGTCTATCAATT-
TAGTCCCTAAGTTAAATGATCGTC TTATTTTGGAT-
TCACAGGTCAATGTCCCGGATCGC-
CAAAGGTGTCTGTGT
TTCCAAGTGTTCCAGACATGTC-
CCCTAAAAAAGTATCTGCAGTGCACAAT GTTTAT-
GTTTCTCCTCTTCGGGGATCAAAGG-
TAAAGAAGATCATAGTGCT
TAACTCTTTATCATGATATGAC-
TAAGTCTTGAGQAGGAGGTAGGTGACAA GAT-
TGTTTGGTTACCTTCCATGTGTTGTGT-
GTTTGCAGATGGATGCTCTTA
TTTCACACAGTACAAAGAGTTACTAT-
GCTTGTGTTGGAGAGTACACAT GCTTACCA-
GAGCCCTTCAAAGGACCTATCTGCCAT-
CAACAACCGCTTGAA
CAAGTAAGTAAAAAAATCACGTCTCT-
CATCAGCTTCTTCCATAAAACCAA TCACTGAC-
CCAATCCAATTTCATCTGGTGTCACAG-
CAGCAGCAGCAACCG
CAAGAGGACGCTAAACTTTGACGCA-
GAAGCAGGGATGGTCAGCGATTCC ATGGTAG-
CAAATAGCCTTAACCTCCAAAAC-
CAAAATCAAAACCAAAATG
GAAGCGATGCATCGTCCTCAGGTGGTGC-
CGCACCCCTTAAAACCGAGCC AACAGATTCATA-
GATATCTCTCTACTTGCTACAC-
CAACTTCTCTTCAGT
TATAGCATCTGTAAATCCTTATGTTGCA-
GAGTTTGCTTTTATGTTTAGCTT TCTAGTTTAT-
AGTGATCACCTCAGGCTATGAGCGGATG-
GATCCCTTTATT GTTTCTTTTTTCTTTTTTTATCTTAGTTAAGTCAGTCTTAATAAGTCATTAATAAATTTACGCCGCAA AACAA-
AAATGTCTTTTTCTTGT-
TCACTCTTTCTAACTGTGTTCGGTGTCCCATCTAC
TAAATTTATTTTCCACTTTAAAAAAAAA-
CAATTTGTGACATTTACTTAACT TGGAACATATA-
CAGTACAGTTAAGCAATTAACTATAAC-
CAACAAATTGTC
TGAACAATTGTCTGTCTTACCTTTT-
CACTTTATGTCGATTTCAGAATAACT-
TACTACTCCAGCATATTTCT
CAAAACTTTCTCAATAGGTTAAATT-
TAAAACAACCTTGCAACTTATGAAA AAATCCTC-
CAGCAAATTTGCCAGAAAAGAATGTTA-
CAATGGCTACAATC ACATCC

What is claimed is:

1. An isolated nucleic acid comprising an RRB polynucleotide selected from the group of polynucleotides consisting of SEQ ID NO: 1, polynucleotides that encode for the polypeptide of SEQ ID NO: 2, and SEQ ID NO: 9.

2. The isolated nucleic acid comprising an RRB polynucleotide of claim 1, wherein said RRB polynucleotide is further selected from the group of polynucleotides consisting of SEQ ID NO: 1, and polynucleotides that encode for the polypeptide of SEQ ID NO: 2, and wherein said nucleic acid further comprises a plant promoter operably linked to said RRB polynucleotide.

3. The isolated nucleic acid of claim 2, wherein said promoter is selected from the group consisting of inducible promoters, tissue-specific promoters, and heterologous promoters.

4. An isolated nucleic acid comprising an RRB polynucleotide selected from the group of polynucleotides that hybridize under highly stringent conditions with the RRB polynucleotide of claim 1, wherein said highly stringent conditions comprise hybridization in 40% formamide, 1 M NaCl concentration, 1% SDS at 37 deg C. and followed by at least one wash in 0.2×SSC at 60 deg C. for 20 minutes.

5. The isolated nucleic acid of claim 4, further comprising a plant promoter operably linked to said RRB polynucleotide.

6. The isolated nucleic acid of claim 5, wherein said promoter is selected from the group consisting of inducible promoters, tissue-specific promoters, and heterologous promoters.

* * * * *

SEQUENCE LISTING

<160> NUMBER OF SEQ ID NOS: 9

<210> SEQ ID NO 1
<211> LENGTH: 3474
<212> TYPE: DNA
<213> ORGANISM: Arabidopsis Thaliana

<400> SEQUENCE: 1

```
gaagtcaggt gaagatagag agagacactg agaggaggga aaatttgtag ggttttcgga      60
gatctctgtg attcctctga atttgtcgaa ttttttcgag gaggcgttag aagtcgggct     120
tcttaaaaat cagatcttct gctcaggctt taatcggcga cgtctggtat tgggatctgt     180
gacacaaaaa gctgcgttgg agactatgga agaagttcag cctccagtga ccccgcccat     240
tgaaccaaat gggaaaagaa gcgaagcctc tctcttggac atatgcgaga aagttctgtc     300
tcttgatggg agcacttgcg atgaagcttt gaagttgttt acagaaacca acgaattttt     360
gtcagcaagc atgtctaaca ttggaagtgg aacgcgggaa gaagtagaga ggttctggtt     420
tgcgtttatt ctctattcag tgaagaggct tagtgtgaga aagaagcgg atggtctgtc      480
agtgtctggt gataatgagt ttaatctatg tcagatactg agggctctga agctaaatat     540
tgtggatttt tttaaagagt tacctcagtt tgtggtcaag gctggatctg tactgggtga     600
actttacggc gcagactggg agaacagact tcaggcaaag gaggtgcagg ctaactttgt     660
gcatcttagc cttctaagca aatactacaa acgtgggttc cgggaattct ttttgacata     720
tgatgcaaac gcagaaaaga actcagcaaa ctcttctacc tatttgctgg atagttatcg     780
ttttggatgg ctactctttt tggcactccg aaaccatgcg tttagtcgat ttaaggacct     840
cgtgacatgc tcaaatggcg tagtttctat attggctatt ttgatcatac atgttccttg     900
tcggtttaga aatttcagca tccaagattc ttctcgcttt gttaagaaag gtgacaaagg     960
tgtagacttg gttgcatcac tttgcaagat atatgacgcc tcagaagatg agttgaggat    1020
agtaattgac aaggcaaata atttggtaga aaccatactg aagaaaaagc catctccagc    1080
atctgagtgc caaactgaca agctagataa tattgaccca gatggcttga cctactttga    1140
ggatttactg gaagagacgt ccatctcaac tagcttaatt acacttgaaa aggattacta    1200
tgatggtaaa ggcgaacttg atgagagggt attcatcaat gaagaggata gcttacttgg    1260
atctggaagc ttatctgcag gagctgttaa tattactggt gttaagagga aaattgatgc    1320
tttgagctca cctgcaagga catttataag cccactttct cctcataagt cgcctgctgc    1380
taagacaaat ggtattagcg gtgctaccaa gttggcagca acaccagtga gcacagcaat    1440
gacaactgcc aagtggctca ggactgtcat atccccgctt ctgccaaaac cttctcctgg    1500
gttggaacat ttccttaaat catgtgatag ggatataaca aatgacgtca cacgaagagc    1560
acacataata ttggaagcta ttttcccaaa tagttcccct ggtgcccaat gtggaggtgg    1620
aagtttgcaa gctgttgacc tgatggatga catatgggca gagcagcgca gattagaagc    1680
```

-continued

```
ttgtaagtta tactacagag ttcttgaggc aatgtgtaaa gcagaagctc agattttgca    1740
tgcaaataat ctgaactctt tattgacaaa tgagaggttc catagatgca tgcttgcttg    1800
ctcagctgaa ttggtactgg ctacccacaa acaattaca atgttgttcc cagctgttct     1860
ggagaggact gggatcacag cctttgatct cagcaaggta attgagagtt tcatacgaca    1920
tgaagattct ctgcctagag agttgagacg acatctgaat tcactggagg aacggcttct    1980
agagagtatg gtatgggaga aggctcttc aatgtacaat tctctgattg ttgccaggcc     2040
atcgcttgca ttggagataa atcagctcgg tttactagct gaaccaatgc catctctgga    2100
tgcaatcgca gcacttatta atttctctga cggagcaaat catgcatcat ctgtacaaaa    2160
gcatgaaact tgtccaggac aaaatggggg gattagatcg cccaaaagat tatgtactga    2220
ttaccgcagc attctagttg aacgcaattc ctttacatca ccagtaaagg atcgtctgtt    2280
ggccttaggc aacgttaaat ccaagatgct gccacctccg ttgcagtctg catttgccag    2340
cccaacacgg cccaacccag gaggtggagg agaaacttgt gcagaaactg gaatcaatat    2400
tttcttcaca aagattaata aattggctgc tgtaagaatc aatggaatgg tggaaagact    2460
acaactttca cagcaaataa gggagagtgt gtattgtttc ttccaacatg tacttgctca    2520
gcggacttct cttttattca gtcgacacat tgaccagatc attctctgtt gcttctacgg    2580
agtggccaag atatcccaaa tgagcctgac tttcagggaa atcatataca actaccggaa    2640
gcaaccacag tgtaaaccat tagttttccg cagcgtttat gtggatgcgt tacaatgtcg    2700
ccgtcaaggg agaatagggc cagatcatgt tgacatcatc acattctaca atgaaatatt    2760
tattcctgcc gtaaagccgc tgctggtgga gctaggtcct gtaagaaacg accgggctgt    2820
ggaagccaat aataagcctg aaggtcaatg tcccggatcg ccaaaggtgt ctgtgtttcc    2880
aagtgttcca gacatgtccc ctaaaaaagt atctgcagtg cacaatgttt atgtttctcc    2940
tcttcgggga tcaaagatgg atgctcttat ttcacacagt acaaagagtt actatgcttg    3000
tgttggagag agtacacatg cttaccagag cccttcaaag gacctatctg ccatcaacaa    3060
ccgcttgaac aacagcagca gcaaccgcaa gaggacgcta aactttgacg cagaagcagg    3120
gatggtcagc gattccatgg tagcaaatag ccttaacctc caaaaccaaa atcaaaacca    3180
aaatggaagc gatgcatcgt cctcaggtgg tgccgcaccc cttaaaaccg agccaacaga    3240
ttcatagata tctctctcta cttgctacac caacttctct tcagttatag catctgtaaa    3300
tccttatgtt gcagagtttg cttttatgtt tagctttcta gtttatagtg atcacctcag    3360
gctatgagcg gatggatccc tttattgttt cttttttctt tttttatctt agttaagtca    3420
gtcttaataa gcattaataa atgtcttttt cttgttcaaa aaaaaaaaa aaaa           3474
```

<210> SEQ ID NO 2
<211> LENGTH: 1013
<212> TYPE: PRT
<213> ORGANISM: Arabidopsis Thaliana

<400> SEQUENCE: 2

```
Met Glu Glu Val Gln Pro Pro Val Thr Pro Pro Ile Glu Pro Asn Gly
 1               5                  10                  15

Lys Arg Ser Glu Ala Ser Leu Leu Asp Ile Cys Glu Lys Val Leu Ser
            20                  25                  30

Leu Asp Gly Ser Thr Cys Asp Glu Ala Leu Lys Leu Phe Thr Glu Thr
        35                  40                  45

Lys Arg Ile Leu Ser Ala Ser Met Ser Asn Ile Gly Ser Gly Thr Arg
    50                  55                  60
```

-continued

```
Glu Glu Val Glu Arg Phe Trp Phe Ala Phe Ile Leu Tyr Ser Val Lys
 65              70                  75                  80

Arg Leu Ser Val Arg Lys Glu Ala Asp Gly Leu Ser Val Ser Gly Asp
             85                  90                  95

Asn Glu Phe Asn Leu Cys Gln Ile Leu Arg Ala Leu Lys Leu Asn Ile
            100                 105                 110

Val Asp Phe Lys Glu Leu Pro Gln Phe Val Val Lys Ala Gly Ser
            115                 120                 125

Val Leu Gly Glu Leu Tyr Gly Ala Asp Trp Glu Asn Arg Leu Gln Ala
    130                 135                 140

Lys Glu Val Gln Ala Asn Phe Val His Leu Ser Leu Leu Ser Lys Tyr
145                 150                 155                 160

Tyr Lys Arg Gly Phe Arg Glu Phe Phe Leu Thr Tyr Asp Ala Asn Ala
                165                 170                 175

Glu Lys Asn Ser Ala Asn Ser Ser Thr Tyr Leu Leu Asp Ser Tyr Arg
                180                 185                 190

Phe Gly Trp Leu Leu Phe Leu Ala Leu Arg Asn His Ala Phe Ser Arg
            195                 200                 205

Phe Lys Asp Leu Val Thr Cys Ser Asn Gly Val Val Ser Ile Leu Ala
210                 215                 220

Ile Leu Ile Ile His Val Pro Cys Arg Phe Arg Asn Phe Ser Ile Gln
225                 230                 235                 240

Asp Ser Ser Arg Phe Val Lys Lys Gly Asp Lys Gly Val Asp Leu Val
                245                 250                 255

Ala Ser Leu Cys Lys Ile Tyr Asp Ala Ser Glu Asp Glu Leu Arg Ile
                260                 265                 270

Val Ile Asp Lys Ala Asn Asn Leu Val Glu Thr Ile Leu Lys Lys Lys
            275                 280                 285

Pro Ser Pro Ala Ser Glu Cys Gln Thr Asp Lys Leu Asp Asn Ile Asp
            290                 295                 300

Pro Asp Gly Leu Thr Tyr Phe Glu Asp Leu Leu Glu Glu Thr Ser Ile
305                 310                 315                 320

Ser Thr Ser Leu Ile Thr Leu Glu Lys Asp Tyr Tyr Asp Gly Lys Gly
                325                 330                 335

Glu Leu Asp Glu Arg Val Phe Ile Asn Glu Glu Asp Ser Leu Leu Gly
                340                 345                 350

Ser Gly Ser Leu Ser Ala Gly Ala Val Asn Ile Thr Gly Val Lys Arg
            355                 360                 365

Lys Ile Asp Ala Leu Ser Ser Pro Ala Arg Thr Phe Ile Ser Pro Leu
            370                 375                 380

Ser Pro His Lys Ser Pro Ala Ala Lys Thr Asn Gly Ile Ser Gly Ala
385                 390                 395                 400

Thr Lys Leu Ala Ala Thr Pro Val Ser Thr Ala Met Thr Thr Ala Lys
                405                 410                 415

Trp Leu Arg Thr Val Ile Ser Pro Leu Leu Pro Lys Pro Ser Pro Gly
                420                 425                 430

Leu Glu His Phe Leu Lys Ser Cys Asp Arg Asp Ile Thr Asn Asp Val
            435                 440                 445

Thr Arg Arg Ala His Ile Ile Leu Glu Ala Ile Phe Pro Asn Ser Ser
            450                 455                 460

Leu Gly Ala Gln Cys Gly Gly Gly Ser Leu Gln Ala Val Asp Leu Met
465                 470                 475                 480
```

```
Asp Asp Ile Trp Ala Glu Gln Arg Arg Leu Glu Ala Cys Lys Leu Tyr
                485                 490                 495

Tyr Arg Val Leu Glu Ala Met Cys Lys Ala Glu Ala Gln Ile Leu His
            500                 505                 510

Ala Asn Asn Leu Asn Ser Leu Leu Thr Asn Glu Arg Phe His Arg Cys
            515                 520                 525

Met Leu Ala Cys Ser Ala Glu Leu Val Leu Ala Thr His Lys Thr Ile
    530                 535                 540

Thr Met Leu Phe Pro Ala Val Leu Glu Arg Thr Gly Ile Thr Ala Phe
545                 550                 555                 560

Asp Leu Ser Lys Val Ile Glu Ser Phe Ile Arg His Glu Asp Ser Leu
            565                 570                 575

Pro Arg Glu Leu Arg Arg His Leu Asn Ser Leu Glu Glu Arg Leu Leu
            580                 585                 590

Glu Ser Met Val Trp Glu Lys Gly Ser Ser Met Tyr Asn Ser Leu Ile
        595                 600                 605

Val Ala Arg Pro Ser Leu Ala Leu Glu Ile Asn Gln Leu Gly Leu Leu
    610                 615                 620

Ala Glu Pro Met Pro Ser Leu Asp Ala Ile Ala Ala Leu Ile Asn Phe
625                 630                 635                 640

Ser Asp Gly Ala Asn His Ala Ser Ser Val Gln Lys His Glu Thr Cys
            645                 650                 655

Pro Gly Gln Asn Gly Gly Ile Arg Ser Pro Lys Arg Leu Cys Thr Asp
            660                 665                 670

Tyr Arg Ser Ile Leu Val Glu Arg Asn Ser Phe Thr Ser Pro Val Lys
        675                 680                 685

Asp Arg Leu Leu Ala Leu Gly Asn Val Lys Ser Lys Met Leu Pro Pro
    690                 695                 700

Pro Leu Gln Ser Ala Phe Ala Ser Pro Thr Arg Pro Asn Pro Gly Gly
705                 710                 715                 720

Gly Gly Glu Thr Cys Ala Glu Thr Gly Ile Asn Ile Phe Phe Thr Lys
            725                 730                 735

Ile Asn Lys Leu Ala Ala Val Arg Ile Asn Gly Met Val Glu Arg Leu
            740                 745                 750

Gln Leu Ser Gln Gln Ile Arg Glu Ser Val Tyr Cys Phe Phe Gln His
        755                 760                 765

Val Leu Ala Gln Arg Thr Ser Leu Leu Phe Ser Arg His Ile Asp Gln
    770                 775                 780

Ile Ile Leu Cys Cys Phe Tyr Gly Val Ala Lys Ile Ser Gln Met Ser
785                 790                 795                 800

Leu Thr Phe Arg Glu Ile Ile Tyr Asn Tyr Arg Lys Gln Pro Gln Cys
            805                 810                 815

Lys Pro Leu Val Phe Arg Ser Val Tyr Val Asp Ala Leu Gln Cys Arg
            820                 825                 830

Arg Gln Gly Arg Ile Gly Pro Asp His Val Asp Ile Ile Thr Phe Tyr
        835                 840                 845

Asn Glu Ile Phe Ile Pro Ala Val Lys Pro Leu Leu Val Glu Leu Gly
850                 855                 860

Pro Val Arg Asn Asp Arg Ala Val Glu Ala Asn Asn Lys Pro Glu Gly
865                 870                 875                 880

Gln Cys Pro Gly Ser Pro Lys Val Ser Val Phe Pro Ser Val Pro Asp
            885                 890                 895

Met Ser Pro Lys Lys Val Ser Ala Val His Asn Val Tyr Val Ser Pro
```

-continued

```
                900              905              910
Leu Arg Gly Ser Lys Met Asp Ala Leu Ile Ser His Ser Thr Lys Ser
            915              920              925
Tyr Tyr Ala Cys Val Gly Glu Ser Thr His Ala Tyr Gln Ser Pro Ser
        930              935              940
Lys Asp Leu Ser Ala Ile Asn Asn Arg Leu Asn Asn Ser Ser Ser Asn
945              950              955              960
Arg Lys Arg Thr Leu Asn Phe Asp Ala Glu Ala Gly Met Val Ser Asp
                965              970              975
Ser Met Val Ala Asn Ser Leu Asn Leu Gln Asn Gln Asn Gln Asn Gln
            980              985              990
Asn Gly Ser Asp Ala Ser Ser Ser Gly Gly Ala Ala Pro  Leu Lys Thr
        995              1000             1005
Glu Pro  Thr Asp Ser
    1010
```

<210> SEQ ID NO 3
<211> LENGTH: 4367
<212> TYPE: DNA
<213> ORGANISM: Zea mays

<400> SEQUENCE: 3

| | | |
|---|---|---|
| tcatctcccg ttcaccccgc gggcgcaggg cgcgctctct cctcgtggcg atcgccgacc | 60 |
| gtagcggccg ctgcccgggt tttcgtcggc cgcttcgcca tgtcttcgct ggacccttcg | 120 |
| ccagcgacga gcacccaaca gaagcaattg agagtttggt taaatctact gacgcaggga | 180 |
| agcaggttct accgcaaagc atataatgaa ctgttctcag gtgtaactac tgagcaggat | 240 |
| ccggattcat cgactaatat tcctgagtat atgcttttg ggtggcatct cttcttaatg | 300 |
| ctccatttga gatcaccaga attgttcaag gacctggtgt cctgcatcca tggattagtt | 360 |
| gctgtgttgg ccatactttt gattcacgtg ccagctaaat ttaggagctt cacgattgaa | 420 |
| ggctcttctc acttaatcaa acaaactgag aaaggcgtgg atcttattgc ttcattatgt | 480 |
| cataactatc atacctctga agaacgtttg aaagaaatgt tgcacaagtc tcacaatgca | 540 |
| atagaagaca ttttccatat gaaagcacta agtgcttcag agtgcaaacc agaaaatttg | 600 |
| gataagatag acacagatga cctgatgtat ttcaaaggtc tgattgatat ggaatgtttc | 660 |
| cagtcaaatt tggaaaaaat ggagaaacta tgtaattcta atagctgtaa aggggagctt | 720 |
| gattttaaat caatttttgat caataatgat tatattcccct atgatgagaa ctcgacgggg | 780 |
| gattccacca atttaggaca ttcaaagtgt gcctttgaaa cattggcatc tcccacaaag | 840 |
| acaataaaga acatgctgac tgttcctagt tctcctttgt caccagccac cggtggttca | 900 |
| gtcaagattg tgcaaatgac accagtaact tctgccatga cgacagctaa gtggcttcgt | 960 |
| gaggtgatat cttcattgcc agataagcct tcatctaagc ttcagcagtt tctgtcatca | 1020 |
| tgcgataggg atttgacaaa tgctgtcaca gaaagggtca gcatagtttt ggaagcaatt | 1080 |
| tttccaacca aatcttctgc caatcggggt gtatcgttag gtctcaattg tgcaaatgcc | 1140 |
| tttgacattc cgtgggcaga agccagaaaa gtggaggctt ccaagttgta ctatagggta | 1200 |
| ttagaggcaa tctgcagagc ggagttacaa aacagcaatg taataatcat aactccattg | 1260 |
| ctgtcaaatg agcgtttcca ccgatgtttg attgcatgtt cagcggactt agtattggcg | 1320 |
| acacataaga cagtcatcat gatgtttcct gctgttcttg agagtaccgg tctaactgca | 1380 |
| tttgatttga gcaaaataat tgagaacttt gtgagacatg aagagaccct cccaagagaa | 1440 |

```
ttgaaaaggc acctaaattc cttagaagaa cagcttttgg aaagcatggc atgggagaaa      1500
ggttcatcat tgtataactc actgattgtt gccaggccat ctgttgcttc agaaataaac      1560
cgccttggtc ttttggctga accaatgcca tctcttgatg acttagtgtc aaggcagaat      1620
gttcgtatcg agggcttgcc tgctacacca tctaaaaaac gtgctgctgg tccagatgac      1680
aacgctgatc ctcgatcacc aaagagatcg tgcaatgaat ctaggaacac agtagtagag      1740
cgcaatttgc agacacctcc acccaagcaa agccacatgg tgtcaactag tttgaaagca      1800
aaatgccatc cactccagtc cacatttgca agtccaactg tctgtaatcc tgttggtggg      1860
aatgaaaaat gtgctgacgt gacaattcat atattctttt ccaagattct gaagttggct      1920
gctattagaa taagaaactt gtgcgaaagg gttcaatgtg tggaacagac agagcgtgtc      1980
tataatgtct tcaagcagat tcttgagcaa cagacaacat tattttttaa tagacacatc      2040
gatcaactta tcctttgctg tctttatggt gttgcaaagg tttgtcaatt agaactcaca      2100
ttcagggaga tactcaacaa ttacaaaaga gaagcacaat gcaagccaga agttttttca      2160
agtatctata ttgggagtac gaaccgtaat ggggtattag tatcgcgcca tgttggtatc      2220 attactttt acaatgaggt atttgttcca gcagcgaagc ctttcctggt gtcactaata      2280
tcatctggta ctcatccaga agacaagaag aatgctagtg ccaaattcc tggatcaccc      2340 aagccatctc ctttcccaaa tttaccagat atgtccccga gaaagtttc agcatctcat      2400 aatgtatatg tgtctccttt gcggcaaacc aagttggatc tactgctgtc accaagttcc      2460
aggagttttt atgcatgcat tggtgaaggc acccatgctt atcagagccc atctaaggat      2520
ttggctgcta taaatagccg cctaaattat aatggcagga aagtaaacag tcgattaaat      2580
ttcgacatgg tgagtgactc agtggtagcc ggcagtctgg gccagataaa tggtggttct      2640
acctcggatc ctgcagctgc atttagcccc cttttcaaaga agagagagac agatacttga      2700
tcaattataa atggtggcct ctctcgtata tagctcacag atccgtgctc cgtagcagtc      2760
tattcttctg aataagtgga ttaactggag cgatttaact gtacatgtat gtgttagtga      2820
gaagcagcag ttttaggca gcaaactgtt tcaagttagc ttttgagcta tcaccatttc      2880
tctgctgatt gaacatatcc gctgtgtaga gtgctaatga atctttagtt ttcattgggc      2940
tgacataaca aatctttatc ctagttggct ggttgttggg aggcattcat cagggttata      3000
tttggttgtc aaaaagtact gtacttaatt cacatctttc acattttca ctagcaatag      3060 cagccccaaa ttgcttttcct gactaggaac atattcttta caggtataag catgccaact      3120
ctaaactata tgaatccttt ttatattctc atttttaagt acttctctgt ttctgctact      3180
tttgtactgt atatttccag cttctccatc agactgatga tcccatattc agtgtgctgc      3240
aagtgatttg acatatgtgg cttatccttc aggtatgtct catgttgtga cttcattgct      3300
gattgctttt gtaatggtac tgttgagttc atttctggtt acaatcagcc tttactgctt      3360
tatattgttc tactaatttt ggcttgcaca gccaggacga ttggttttct gcatcaatca      3420
atctttttta ggacaagata tttttgtatg ctacacttcc caaattgcaa ttaatccaga      3480
agtctacctt gttttattct attagttctc agcaacagtg aatgaatatg aatcagtcat      3540
gctgatagat gttcatctgg ttattccaaa caatctgaca tcgcatctct ttctgcaagt      3600
gagatgaaga aaacctgaaa tgctatcacc atttaaaaca ttggcttctg aagttcaggt      3660
gattagcagg agacgttctg acattgccat tgacatgtac ggtagtgatg caggagacg      3720 ttcttaaaca gcagctgctc cttcagcttg taatgtctga ttgtattgac caagagcatc      3780 cacccttgcct tatggtacta actgaatgag ctggtgacgc tgactcatct gcataatggc      3840
```

-continued

```
agatgcttaa ccatctttag gagctcatgt catgattcca gctgcaccgt gtgcaaatgt    3900
gaaggccctg caagggcttt ccaggccgca ccaatcctgc ttgcttcttg aagtacata     3960 tggtgccacc taaataaaag ctgtttctgg ttatgtctgt ccttgacatg tcaacagatt    4020
agtgttgggt tgcagtcgtg tggtgtttaa gtcttggaga aggcgagaag tcattgctgc    4080
cagcattgtg tcgtcaggca cagaagtact caaaagtgag agctactttg ttgcgagcaa    4140
acggagggcg ataggttg atagccaatt tcagttctct atatacaagc agcggatttt     4200
gtttagagtt agcttttgag atgcatcatt tctttcacat ctgattctgt gtgttgtaac    4260
tcggagtcgc gtagaagtta gaatgctaac tgacccttaa ttttcaccga ataatttgct    4320
agcgtttttc agtatgaaaa aaaaaaaaaa aaaaaaaaaa aaaaaaa                  4367
```

<210> SEQ ID NO 4
<211> LENGTH: 866
<212> TYPE: PRT
<213> ORGANISM: Zea Mays

<400> SEQUENCE: 4

```
Met Ser Ser Leu Asp Pro Ser Pro Ala Thr Ser Thr Gln Gln Lys Gln
1               5                   10                  15

Leu Glu Ser Leu Val Asn Leu Leu Thr Gln Gly Ser Arg Phe Tyr Arg
            20                  25                  30

Lys Ala Tyr Asn Glu Leu Phe Ser Gly Val Thr Thr Glu Gln Asp Pro
        35                  40                  45

Asp Ser Ser Thr Asn Ile Pro Glu Tyr Met Leu Phe Gly Trp His Leu
    50                  55                  60

Phe Leu Met Leu His Leu Arg Ser Pro Glu Leu Phe Lys Asp Leu Val
65                  70                  75                  80

Ser Cys Ile His Gly Leu Val Ala Val Leu Ala Ile Leu Leu Ile His
                85                  90                  95

Val Pro Ala Lys Phe Arg Ser Phe Thr Ile Glu Gly Ser Ser His Leu
            100                 105                 110

Ile Lys Gln Thr Glu Lys Gly Val Asp Leu Ile Ala Ser Leu Cys His
        115                 120                 125

Asn Tyr His Thr Ser Glu Glu Arg Leu Lys Glu Met Leu His Lys Ser
    130                 135                 140

His Asn Ala Ile Glu Asp Ile Phe His Met Lys Ala Leu Ser Ala Ser
145                 150                 155                 160

Glu Cys Lys Pro Glu Asn Leu Asp Lys Ile Asp Thr Asp Leu Met
                165                 170                 175

Tyr Phe Lys Gly Leu Ile Asp Met Glu Cys Phe Gln Ser Asn Leu Glu
            180                 185                 190

Lys Met Glu Lys Leu Cys Asn Ser Asn Ser Cys Lys Gly Glu Leu Asp
        195                 200                 205

Phe Lys Ser Ile Leu Ile Asn Asn Asp Tyr Ile Pro Tyr Asp Glu Asn
    210                 215                 220

Ser Thr Gly Asp Ser Thr Asn Leu Gly His Ser Lys Cys Ala Phe Glu
225                 230                 235                 240

Thr Leu Ala Ser Pro Thr Lys Thr Ile Lys Asn Met Leu Thr Val Pro
                245                 250                 255

Ser Ser Pro Leu Ser Pro Ala Thr Gly Gly Ser Val Lys Ile Val Gln
            260                 265                 270

Met Thr Pro Val Thr Ser Ala Met Thr Thr Ala Lys Trp Leu Arg Glu
```

```
            275                 280                 285
Val Ile Ser Ser Leu Pro Asp Lys Pro Ser Lys Leu Gln Gln Phe
    290                 295                 300

Leu Ser Ser Cys Asp Arg Asp Leu Thr Asn Ala Val Thr Glu Arg Val
305                 310                 315                 320

Ser Ile Val Leu Glu Ala Ile Phe Pro Thr Lys Ser Ser Ala Asn Arg
                325                 330                 335

Gly Val Ser Leu Gly Leu Asn Cys Ala Asn Ala Phe Asp Ile Pro Trp
                340                 345                 350

Ala Glu Ala Arg Lys Val Glu Ala Ser Lys Leu Tyr Tyr Arg Val Leu
                355                 360                 365

Glu Ala Ile Cys Arg Ala Glu Leu Gln Asn Ser Asn Val Asn Asn Leu
    370                 375                 380

Thr Pro Leu Leu Ser Asn Glu Arg Phe His Arg Cys Leu Ile Ala Cys
385                 390                 395                 400

Ser Ala Asp Leu Val Leu Ala Thr His Lys Thr Val Ile Met Met Phe
                405                 410                 415

Pro Ala Val Leu Glu Ser Thr Gly Leu Thr Ala Phe Asp Leu Ser Lys
                420                 425                 430

Ile Ile Glu Asn Phe Val Arg His Glu Glu Thr Leu Pro Arg Glu Leu
    435                 440                 445

Lys Arg His Leu Asn Ser Leu Glu Glu Gln Leu Leu Glu Ser Met Ala
    450                 455                 460

Trp Glu Lys Gly Ser Ser Leu Tyr Asn Ser Leu Ile Val Ala Arg Pro
465                 470                 475                 480

Ser Val Ala Ser Glu Ile Asn Arg Leu Gly Leu Leu Ala Glu Pro Met
                485                 490                 495

Pro Ser Leu Asp Asp Leu Val Ser Arg Gln Asn Val Arg Ile Glu Gly
                500                 505                 510

Leu Pro Ala Thr Pro Ser Lys Lys Arg Ala Ala Gly Pro Asp Asp Asn
                515                 520                 525

Ala Asp Pro Arg Ser Pro Lys Arg Ser Cys Asn Glu Ser Arg Asn Thr
    530                 535                 540

Val Val Glu Arg Asn Leu Gln Thr Pro Pro Lys Gln Ser His Met
545                 550                 555                 560

Val Ser Thr Ser Leu Lys Ala Lys Cys His Pro Leu Gln Ser Thr Phe
                565                 570                 575

Ala Ser Pro Thr Val Cys Asn Pro Val Gly Asn Glu Lys Cys Ala
                580                 585                 590

Asp Val Thr Ile His Ile Phe Phe Ser Lys Ile Leu Lys Leu Ala Ala
                595                 600                 605

Ile Arg Ile Arg Asn Leu Cys Glu Arg Val Gln Cys Val Glu Gln Thr
    610                 615                 620

Glu Arg Val Tyr Asn Val Phe Lys Gln Ile Leu Glu Gln Thr Thr
625                 630                 635                 640

Leu Phe Phe Asn Arg His Ile Asp Gln Leu Ile Leu Cys Cys Leu Tyr
                645                 650                 655

Gly Val Ala Lys Val Cys Gln Leu Glu Leu Thr Phe Arg Glu Ile Leu
                660                 665                 670

Asn Asn Tyr Lys Arg Glu Ala Gln Cys Lys Pro Glu Val Phe Ser Ser
                675                 680                 685

Ile Tyr Ile Gly Ser Thr Asn Arg Asn Gly Val Leu Val Ser Arg His
    690                 695                 700
```

```
Val Gly Ile Ile Thr Phe Tyr Asn Glu Val Phe Pro Ala Ala Lys
705                 710                 715                 720

Pro Phe Leu Val Ser Leu Ile Ser Ser Gly Thr His Pro Glu Asp Lys
            725                 730                 735

Lys Asn Ala Ser Gly Gln Ile Pro Gly Ser Pro Lys Pro Ser Pro Phe
            740                 745                 750

Pro Asn Leu Pro Asp Met Ser Pro Lys Lys Val Ser Ala Ser His Asn
            755                 760                 765

Val Tyr Val Ser Pro Leu Arg Gln Thr Lys Leu Asp Leu Leu Leu Ser
            770                 775                 780

Pro Ser Ser Arg Ser Phe Tyr Ala Cys Ile Gly Glu Gly Thr His Ala
785                 790                 795                 800

Tyr Gln Ser Pro Ser Lys Asp Leu Ala Ala Ile Asn Ser Arg Leu Asn
            805                 810                 815

Tyr Asn Gly Arg Lys Val Asn Ser Arg Leu Asn Phe Asp Met Val Ser
            820                 825                 830

Asp Ser Val Val Ala Gly Ser Leu Gly Gln Ile Asn Gly Gly Ser Thr
            835                 840                 845

Ser Asp Pro Ala Ala Ala Phe Ser Pro Leu Ser Lys Lys Arg Glu Thr
    850                 855                 860

Asp Thr
865

<210> SEQ ID NO 5
<211> LENGTH: 2945
<212> TYPE: DNA
<213> ORGANISM: Zea mays

<400> SEQUENCE: 5
gagaattgaa aagacaccta aattccttag aagaacaaat tttggaaagc atggcatggg      60
agaaaggttc atcattgtat aactcactga ttgttgccag ccatctgtt gcttcagaaa     120 ttaatcgctt tggtcttctg gctgaatcaa tgccatctct tgatgactta gtggcaaggc     180
agaatattca tattgagggc ttgcctgcta caccatctaa aaaacgtgct gctggtcgag     240
acgacaatgc tgatcctcga tcaccaaaga gaccatgcaa tgaatctagg agcacagtag     300
tagaacacaa tttgcagaca cctccaccca agcaatgcca catggtgttg actagtttga     360
aagcaaaatg ccatccactc cagtccacat ttgcaagtcc aactgtcagt aatcctgttg     420
gtgggaacga aaatgtgct gacgtgacaa ttcagatatt cttttccaaa attctgaagt     480
tagctgctat tagaataaga aacttgtgtg aaaggattca atatatggaa cagacagagc     540
gtgtctataa tgtcttcaag cagattcttg atcaacagac aacattattt tttaatagac     600
acatgcatca acttattctt tgctgtcttt atggtgttgc aaaggtttgc caattagaac     660
tctcattcag ggagatactc aacaattaca aaaagaagc acaatgcaaa ccagaagttt     720
ttttaagcat ctatattgga agtaggaatc ataatgggt attaatatca cgccatgttg     780
atatcattac tttttacaat gaggtctttg ttccagcagc caagcctttc ctggtgtcat     840
taatatcatc tggtactcgt ccagaagaca agaagaatgc tagtggccaa gttcctggat     900
caccgaagct atctcctttc ccaaatttac cagatatgtc cccaagaaaa gtttcagctt     960
ctcataatgt atatgtgtct cctttgcggc aaaccaagat ggatttactg ctgtcaccaa    1020
gttccaggag tttttatgca tgcattggtg aaggcaccca tgcttatcag agcccatcta    1080
aagatttggc tgctataaat agccgcctaa attataatgg tcggagagta aacagtcgat    1140
```

-continued

```
taaactttga catggtgagc gactcagtgg tagctggtag tctaggccag ccaaatggtg      1200
gttctacttc cttggatcct gcagctgcat ttagccccct ttcaaagaga aagccagata      1260
cttgatcaaa tataaatggc gatctctctc gtatatagct cacagctcca tagcagtcta      1320
ttcttctgaa taagtgggtt gactggagtg atttaactgt acatgtatgt gttagtgaga      1380
accagcagtt tataggcagc aaactgtttt aaattagctt tgaggtttta tcaccatttc      1440
cctgctgatt gaacatattt tagattgtaa catctgcttt gtagaatgct aatgaatctt      1500
tagttttcag tgggttgaca ttaaaaatcc ttatcctagt tggctggttg ttgggagaca      1560
ttcatcaagg ttatatttgg tcgtcaaata gtactgtact tgattcatat ctttcatatt      1620
tttcactagc gttggcaacc gtaaattgct ttcctgacta ggaacatatt cttcacaagt      1680
atggcaactc taaactattt gaccttttat attctcattt ttaagtactt tctctatttc      1740
tgctactttt gtactgtgta tttccagctt ctccaccaga ctgattgtta gagtgtatgc      1800
tcctatatta tccatgtatg tgtaaatggg ctgctagccc attagggtta ggttcccctg      1860
ggtctatata tgtaaccacc ctctatgcaa tagaagttga atatcagttt ctatcactaa      1920
tgattccata ttcagtgggc tgcaagtgat ttgacatacg tgccttatcc ttcaggtatg      1980
tctcatgttg actttgcttt tgtaatggta ctgttggctt cattgctgga atgctggtta      2040
taatcaacct ttactgctct atattgttct ttttttggtt tgcacaacca gggtggttgg      2100
ttttctgaat caatcaatcc atttcctcgg acgacaagaa aatttttgta tgttacactt      2160
cccaaaattg caattaattc agaagtctgc ctactttcat tcagttagtt ctcagcaaca      2220
ctgaaaggat atgaatcagt caacccgata gatgtttatc tggttattcc aaacaatctg      2280
acatcacatc tgtttctgca ggcgagataa ggaaaatctg aaatgctatc accatttaaa      2340
acattggctc ctggaagttc aggtaggtgt tgctgtagaa tgagatggtt aggaatcttt      2400
acaagctcag gctatatgat ttcagcagca ctgtaacctg gggtgcaaat gttaaggccc      2460
tgcaagcact ttccaggcca caccaattct gcttggttct tgaagataca ttcttcctat      2520
gtgcccccta tataaaagcc atttctggtt gttatgttta tccttgacat gtcaacagat      2580
tagtgttggg ttgcagtcat gcggtcctta agtctcggag aaggcgagaa gtcattgctg      2640
ctagcattgt gatcgtcggc cacgaaagta atcaaaaagt gagagctact tgttcctagc      2700
aaatggagaa gggcgatata taggtttatg atcaaattca gtgtatgcaa gcagcatatt      2760
ttgtttagag ttagcttttg aggttcatca tttcatttca cagctgattc tctatgttgt      2820
aactccttag tcgtgtagaa attagaatgc tatctgctta attttagtg aataatttgc      2880 tagtatattt ttgaatgtaa ttgcagtagc tctgcctctt cattaaggaa aaaaaaaaa      2940 aaaaa                                                                  2945
```

<210> SEQ ID NO 6
<211> LENGTH: 420
<212> TYPE: PRT
<213> ORGANISM: Zea mays

<400> SEQUENCE: 6

```
Glu Leu Lys Arg His Leu Asn Ser Leu Glu Glu Gln Ile Leu Glu Ser
 1               5                  10                  15

Met Ala Trp Glu Lys Gly Ser Ser Leu Tyr Asn Ser Leu Ile Val Ala
            20                  25                  30

Arg Pro Ser Val Ala Ser Glu Ile Asn Arg Phe Gly Leu Leu Ala Glu
        35                  40                  45
```

```
Ser Met Pro Ser Leu Asp Asp Leu Val Ala Arg Gln Asn Ile His Ile
    50                  55                  60
Glu Gly Leu Pro Ala Thr Pro Ser Lys Lys Arg Ala Ala Gly Arg Asp
 65                  70                  75                  80
Asp Asn Ala Asp Pro Arg Ser Pro Lys Arg Pro Cys Asn Glu Ser Arg
                 85                  90                  95
Ser Thr Val Val Glu His Asn Leu Gln Thr Pro Pro Lys Gln Cys
            100                 105                 110
His Met Val Leu Thr Ser Leu Lys Ala Lys Cys His Pro Leu Gln Ser
        115                 120                 125
Thr Phe Ala Ser Pro Thr Val Ser Asn Pro Val Gly Gly Asn Glu Lys
    130                 135                 140
Cys Ala Asp Val Thr Ile Gln Ile Phe Phe Ser Lys Ile Leu Lys Leu
145                 150                 155                 160
Ala Ala Ile Arg Ile Arg Asn Leu Cys Glu Arg Ile Gln Tyr Met Glu
                165                 170                 175
Gln Thr Glu Arg Val Tyr Asn Val Phe Lys Gln Ile Leu Asp Gln Gln
            180                 185                 190
Thr Thr Leu Phe Phe Asn Arg His Met His Gln Leu Ile Leu Cys Cys
        195                 200                 205
Leu Tyr Gly Val Ala Lys Val Cys Gln Leu Glu Leu Ser Phe Arg Glu
    210                 215                 220
Ile Leu Asn Asn Tyr Lys Lys Glu Ala Gln Cys Lys Pro Glu Val Phe
225                 230                 235                 240
Leu Ser Ile Tyr Ile Gly Ser Arg Asn His Asn Gly Val Leu Ile Ser
                245                 250                 255
Arg His Val Asp Ile Ile Thr Phe Tyr Asn Glu Val Phe Val Pro Ala
            260                 265                 270
Ala Lys Pro Phe Leu Val Ser Leu Ile Ser Ser Gly Thr Arg Pro Glu
        275                 280                 285
Asp Lys Lys Asn Ala Ser Gly Gln Val Pro Gly Ser Pro Lys Leu Ser
    290                 295                 300
Pro Phe Pro Asn Leu Pro Asp Met Ser Pro Lys Lys Val Ser Ala Ser
305                 310                 315                 320
His Asn Val Tyr Val Ser Pro Leu Arg Gln Thr Lys Met Asp Leu Leu
                325                 330                 335
Leu Ser Pro Ser Ser Arg Ser Phe Tyr Ala Cys Ile Gly Glu Gly Thr
            340                 345                 350
His Ala Tyr Gln Ser Pro Ser Lys Asp Leu Ala Ala Ile Asn Ser Arg
        355                 360                 365
Leu Asn Tyr Asn Gly Arg Arg Val Asn Ser Arg Leu Asn Phe Asp Met
    370                 375                 380
Val Ser Asp Ser Val Val Ala Gly Ser Leu Gly Gln Pro Asn Gly Gly
385                 390                 395                 400
Ser Thr Ser Leu Asp Pro Ala Ala Ala Phe Ser Pro Leu Ser Lys Arg
                405                 410                 415
Lys Pro Asp Thr
            420

<210> SEQ ID NO 7
<211> LENGTH: 2538
<212> TYPE: DNA
<213> ORGANISM: Zea mays
```

<400> SEQUENCE: 7

```
cctagttccc ctttgtcacc caccaacggt ggttcagtca agattgtgca aatgacacca      60
ataacttctg ccatgacgac agctaagtgg cttcgtgagg tgatatcttc attgccagag     120
aagccttcat ctaagcttca gcagttgatg tcatcatgcg atagagattt gacaaatgcc     180
gtcacagaaa gggtcagcat agttctggaa gcaattttc caaccaagtc ttctgctgat      240
cggggtggct cattaggcct caattgtgca aatgcctttg atactctatg ggcagatgcc     300
agaaaaatgg aggcttccaa gttgtactat agggtattag aggcaatctg cagagctgag     360
ttacaaaaca gcaatgtaaa caatctaact ccattgctgt caaatgagcg ttttcaccga     420
tgtttgattg catgttcagc ggagctagta ttggcgacac ataagacggt catcatgatg     480
tttcctgctg ttcttgagag tactggtcta acctcatttg atttgagcaa ataattgag      540
aactttgtga acatgaaga gaccctccca agagaattga aaagacacct aaattcctta      600
gaagaacaaa ttttggaaag catggcatgg gagaaaggtt catcattgta taactcactg     660
attgttgcca ggccatctgt tgcttcagaa attaatcgct ttggtcttct ggctgaatca     720
atgccatctc ttgatgactt agtggcaagg cagaatattc atattgaggg cttgcctgct     780
acaccatcta aaaaacgtgc tgctggtcga gacgacaatg ctgatcctcg atcaccaaag     840
agaccatgca atgaatctag gagcacagta gtagaacaca atttgcagac acctccaccc     900
aagcaatgcc acatggtgtt gactagtttg aaagcaaaat gccatccact ccagtccaca     960
tttgcaagtc caactgtcag taatcctgtt ggtgggaacg aaaatgtgc tgacgtgaca     1020
attcagatat tcttttccaa aattctgaag ttagctgcta ttagaataag aaacttgtgt    1080
gaaaggattc aatatatgga acagacagag cgtgtctata atgtcttcaa gcagattctt    1140
gatcaacaga caacattatt ttttaataga cacatgcatc aacttattct ttgctgtctt    1200
tatggtgttg caaggtttg ccaattagaa ctctcattca gggagatact caacaattac     1260
aaaaagaag cacaatgcaa accagaagtt tttttaagca tctatattgg aagtaggaat     1320
cataatgggg tattaatatc acgccatgtt gatatcatta ctttttacaa tgaggtcttt     1380
gttccagcag ccaagccttt cctggtgtca ttaatatcat ctggtactcg tccagaagac    1440
aagaagaatg ctagtggcca agttcctgga tcaccgaagc tatctccttt cccaaattta    1500
ccagatatgt ccccaaagaa agtttcagct tctcataatg tatatgtgtc tcctttgcgg    1560
caaaccaaga tggatttact gctgtcacca agttccagga gtttttatgc atgcattggt    1620
gaaggcaccc atgcttatca gagcccatct aaagatttgg ctgctataaa tagccgccta    1680
aattataatg gtcggagagt aaacagtcga ttaaactttg acatggtatg tctcatgttg    1740
actttgcttt tgtaatggta ctgttggctt cattgctgga atgctggtta taatcaacct    1800
ttactgctct atattgttct ttttttggtt tgcacaacca gggtggttgg ttttctgaat    1860
caatcaatcc atttcctcgg acacaagata atttttgcga gataaggaaa atctgaaatg    1920
ctatcaccat ttaaaacatt ggctcctgga agttcaggtt aggtgttgct gtagaatgag    1980
atggttacca tctttacaag ctcaggctat atgatttcag cagcactgta acctggggtg    2040
caaatgttaa ggccctgcaa gcactttcca ggccacacca attctgcttg gttcttgaag    2100
atacattctt cctatgtgcc ccctatataa aagccatttc tggttgttat gtttatcctt    2160
gacatgtcaa cagattagtg ttgggttgca gtcatgcggt ccttaagtct cggagaaggc    2220
gagaagtcat tgctgctagc attgtgatcg tcggccacga agtaatcaa aaagtgagag     2280
ctacttgttc ctagcaaatg gagaagggcg atatataggt ttatgatcaa attcagtgta    2340
```

```
tgcaagcagc atattttgtt tagagttagc ttttgaggtt catcatttca tttcacagct    2400
gattctctat gttgtaactc cttagtcgtg tagaaattag aatgctatct gcttaatttt    2460
tagtgaataa tttgctagta tattttgaa tgtaattgca gtagctctgc ctcttcatta     2520
aaaaaaaaaa aaaaaaaa                                                   2538
```

<210> SEQ ID NO 8
<211> LENGTH: 584
<212> TYPE: PRT
<213> ORGANISM: Zea mays

<400> SEQUENCE: 8

```
Pro Ser Ser Pro Leu Ser Pro Thr Asn Gly Gly Ser Val Lys Ile Val
 1               5                  10                  15

Gln Met Thr Pro Ile Thr Ser Ala Met Thr Thr Ala Lys Trp Leu Arg
             20                  25                  30

Glu Val Ile Ser Ser Leu Pro Glu Lys Pro Ser Ser Lys Leu Gln Gln
         35                  40                  45

Leu Met Ser Ser Cys Asp Arg Asp Leu Thr Asn Ala Val Thr Glu Arg
 50                  55                  60

Val Ser Ile Val Leu Glu Ala Ile Phe Pro Thr Lys Ser Ser Ala Asp
65                  70                  75                  80

Arg Gly Gly Ser Leu Gly Leu Asn Cys Ala Asn Ala Phe Asp Thr Leu
                 85                  90                  95

Trp Ala Asp Ala Arg Lys Met Glu Ala Ser Lys Leu Tyr Tyr Arg Val
            100                 105                 110

Leu Glu Ala Ile Cys Arg Ala Glu Leu Gln Asn Ser Asn Val Asn Asn
        115                 120                 125

Leu Thr Pro Leu Leu Ser Asn Glu Arg Phe His Arg Cys Leu Ile Ala
    130                 135                 140

Cys Ser Ala Glu Leu Val Leu Ala Thr His Lys Thr Val Ile Met Met
145                 150                 155                 160

Phe Pro Ala Val Leu Glu Ser Thr Gly Leu Thr Ser Phe Asp Leu Ser
                165                 170                 175

Lys Ile Ile Glu Asn Phe Val Arg His Glu Glu Thr Leu Pro Arg Glu
            180                 185                 190

Leu Lys Arg His Leu Asn Ser Leu Glu Glu Gln Ile Leu Glu Ser Met
        195                 200                 205

Ala Trp Glu Lys Gly Ser Ser Leu Tyr Asn Ser Leu Ile Val Ala Arg
    210                 215                 220

Pro Ser Val Ala Ser Glu Ile Asn Arg Phe Gly Leu Leu Ala Glu Ser
225                 230                 235                 240

Met Pro Ser Leu Asp Asp Leu Val Ala Arg Gln Asn Ile His Ile Glu
                245                 250                 255

Gly Leu Pro Ala Thr Pro Ser Lys Lys Arg Ala Ala Gly Arg Asp Asp
            260                 265                 270

Asn Ala Asp Pro Arg Ser Pro Lys Arg Pro Cys Asn Glu Ser Arg Ser
        275                 280                 285

Thr Val Val Glu His Asn Leu Gln Thr Pro Pro Lys Gln Cys His
    290                 295                 300

Met Val Leu Thr Ser Leu Lys Ala Lys Cys His Pro Leu Gln Ser Thr
305                 310                 315                 320

Phe Ala Ser Pro Thr Val Ser Asn Pro Val Gly Gly Asn Glu Lys Cys
                325                 330                 335
```

```
Ala Asp Val Thr Ile Gln Ile Phe Phe Ser Lys Ile Leu Lys Leu Ala
            340                 345                 350

Ala Ile Arg Ile Arg Asn Leu Cys Glu Arg Ile Gln Tyr Met Glu Gln
            355                 360                 365

Thr Glu Arg Val Tyr Asn Val Phe Lys Gln Ile Leu Asp Gln Gln Thr
        370                 375                 380

Thr Leu Phe Phe Asn Arg His Met His Gln Leu Ile Leu Cys Cys Leu
385                 390                 395                 400

Tyr Gly Val Ala Lys Val Cys Gln Leu Glu Leu Ser Phe Arg Glu Ile
                405                 410                 415

Leu Asn Asn Tyr Lys Lys Glu Ala Gln Cys Lys Pro Glu Val Phe Leu
            420                 425                 430

Ser Ile Tyr Ile Gly Ser Arg Asn His Asn Gly Val Leu Ile Ser Arg
        435                 440                 445

His Val Asp Ile Ile Thr Phe Tyr Asn Glu Val Phe Val Pro Ala Ala
        450                 455                 460

Lys Pro Phe Leu Val Ser Leu Ile Ser Ser Gly Thr Arg Pro Glu Asp
465                 470                 475                 480

Lys Lys Asn Ala Ser Gly Gln Val Pro Gly Ser Pro Lys Leu Ser Pro
                485                 490                 495

Phe Pro Asn Leu Pro Asp Met Ser Pro Lys Lys Val Ser Ala Ser His
            500                 505                 510

Asn Val Tyr Val Ser Pro Leu Arg Gln Thr Lys Met Asp Leu Leu Leu
            515                 520                 525

Ser Pro Ser Ser Arg Ser Phe Tyr Ala Cys Ile Gly Glu Gly Thr His
        530                 535                 540

Ala Tyr Gln Ser Pro Ser Lys Asp Leu Ala Ala Ile Asn Ser Arg Leu
545                 550                 555                 560

Asn Tyr Asn Gly Arg Arg Val Asn Ser Arg Leu Asn Phe Asp Met Val
                565                 570                 575

Cys Leu Met Leu Thr Leu Leu Leu
            580

<210> SEQ ID NO 9
<211> LENGTH: 6422
<212> TYPE: DNA
<213> ORGANISM: Arabidopsis Thaliana
<220> FEATURE:
<221> NAME/KEY: promoter
<222> LOCATION: (1)..(543)
<223> OTHER INFORMATION:
<221> NAME/KEY: 5'UTR
<222> LOCATION: (544)..(653)
<223> OTHER INFORMATION:
<221> NAME/KEY: Intron
<222> LOCATION: (654)..(1093)
<223> OTHER INFORMATION:
<221> NAME/KEY: 5'UTR
<222> LOCATION: (1094)..(1107)
<223> OTHER INFORMATION:
<221> NAME/KEY: exon
<222> LOCATION: (1108)..(1189)
<223> OTHER INFORMATION:
<221> NAME/KEY: Intron
<222> LOCATION: (1190)..(1307)
<223> OTHER INFORMATION:
<221> NAME/KEY: exon
<222> LOCATION: (1308)..(1410)
<223> OTHER INFORMATION:
<221> NAME/KEY: Intron
<222> LOCATION: (1411)..(1497)
<223> OTHER INFORMATION:
```

-continued

```
<221> NAME/KEY: exon
<222> LOCATION: (1498)..(1641)
<223> OTHER INFORMATION:
<221> NAME/KEY: Intron
<222> LOCATION: (1642)..(1721)
<223> OTHER INFORMATION:
<221> NAME/KEY: exon
<222> LOCATION: (1722)..(1817)
<223> OTHER INFORMATION:
<221> NAME/KEY: Intron
<222> LOCATION: (1818)..(1902)
<223> OTHER INFORMATION:
<221> NAME/KEY: exon
<222> LOCATION: (1903)..(1951)
<223> OTHER INFORMATION:
<221> NAME/KEY: Intron
<222> LOCATION: (1952)..(2216)
<223> OTHER INFORMATION:
<221> NAME/KEY: exon
<222> LOCATION: (2217)..(2409)
<223> OTHER INFORMATION:
<221> NAME/KEY: Intron
<222> LOCATION: (2410)..(2540)
<223> OTHER INFORMATION:
<221> NAME/KEY: exon
<222> LOCATION: (2541)..(2606)
<223> OTHER INFORMATION:
<221> NAME/KEY: Intron
<222> LOCATION: (2607)..(2693)
<223> OTHER INFORMATION:
<221> NAME/KEY: exon
<222> LOCATION: (2694)..(2873)
<223> OTHER INFORMATION:
<221> NAME/KEY: Intron
<222> LOCATION: (2874)..(2973)
<223> OTHER INFORMATION:
<221> NAME/KEY: exon
<222> LOCATION: (2974)..(4029)
<223> OTHER INFORMATION:
<221> NAME/KEY: Intron
<222> LOCATION: (4030)..(4124)
<223> OTHER INFORMATION:
<221> NAME/KEY: exon
<222> LOCATION: (4125)..(4287)
<223> OTHER INFORMATION:
<221> NAME/KEY: Intron
<222> LOCATION: (4288)..(4385)
<223> OTHER INFORMATION:
<221> NAME/KEY: exon
<222> LOCATION: (4386)..(4458)
<223> OTHER INFORMATION:
<221> NAME/KEY: Intron
<222> LOCATION: (4459)..(4579)
<223> OTHER INFORMATION:
<221> NAME/KEY: exon
<222> LOCATION: (4580)..(4756)
<223> OTHER INFORMATION:
<221> NAME/KEY: Intron
<222> LOCATION: (4757)..(4869)
<223> OTHER INFORMATION:
<221> NAME/KEY: exon
<222> LOCATION: (4870)..(4969)
<223> OTHER INFORMATION:
<221> NAME/KEY: Intron
<222> LOCATION: (4970)..(5051)
<223> OTHER INFORMATION:
<221> NAME/KEY: exon
<222> LOCATION: (5052)..(5184)
<223> OTHER INFORMATION:
<221> NAME/KEY: Intron
<222> LOCATION: (5185)..(5276)
<223> OTHER INFORMATION:
<221> NAME/KEY: exon
<222> LOCATION: (5277)..(5390)
<223> OTHER INFORMATION:
<221> NAME/KEY: Intron
<222> LOCATION: (5391)..(5497)
<223> OTHER INFORMATION:
<221> NAME/KEY: exon
```

-continued

```
<222> LOCATION: (5498)..(5613)
<223> OTHER INFORMATION:
<221> NAME/KEY: Intron
<222> LOCATION: (5614)..(5695)
<223> OTHER INFORMATION:
<221> NAME/KEY: exon
<222> LOCATION: (5696)..(5870)
<223> OTHER INFORMATION:
<221> NAME/KEY: 3'UTR
<222> LOCATION: (5871)..(6081)
<223> OTHER INFORMATION:
<221> NAME/KEY: misc_feature
<222> LOCATION: (6082)..(6421)
<223> OTHER INFORMATION:

<400> SEQUENCE: 9
gatcctactc acactcgaag atgacgaaga agacttaatc tgaatccatc cgcggatagg      60
acactcatac ttctgcaacc aaacgttcta caatggcaaa tatgtaattt cccgcgtgac     120
ctaaactaga aacggcatcg tattaagggt gggcccaatc ataactcaca cgaggctttg     180
tcgcggtcac gaaaacccag acggcgttaa tgcccactc cgtttgtttc daccccgccg     240
tgacggcgaa tctttccctc tcagcgtttc acgcaacagt aagtaagttt tggcggtaaa     300
attgggtcac agatgggtac gtgtcgattt aatagtggtt gaaagcgcgc gaatataatt     360
gtatacgtat gtgtatgtat tctccgtgtt gtttttcccg cgcgagatat atccttttt      420 agggttttgcc gcataatcag accccattct agagagagaa gagggaagtc aggtgaagat    480
agagagagac actgagagga gggaaaattt gtagggtttc cggagatctc tgtgattcct    540
ctgaatttgt cgaattttt ggaggaggcg ttagaagtcg ggcttcttaa aaatcagatc     600
ttctgctcag ctttaatcgg cgacgtctgg tattgggatc tgtgacacaa aaaggtaaga    660
tctttctcta ttgcctatcc tttgatttga atcttatcc tctaggtggt ttatctgaaa     720
ttttctattg atatttcgct attcgattgt aagttggtga gagaattctc caaaacaaa     780 aaagagaaaa actttgaatg aatatttaag ataacatctg ggtaaaattt ttccggagtg    840 gtgggttta dattatgccc caattctct tcttttttc ccccaaattt tgtctttctg      900
ccatgttttg ggaaattggg agtttgtttt ctcatgtctg ttagtgtgtt cttccgaatg    960
ggttgggcat ggttcctatt gaatttcagt gtgattaaat taacaaatct ctttgcttga   1020
aaagtcccct tttcttcgtc ttcagttagc agtttaattg gaagtaaaat tagcttgatt   1080
ttgcatgttt tcagctgcgt tggagac tat gga aga agt tca gcc tcc agt gac   1134
                                Tyr Gly Arg Ser Ser Ala Ser Ser Asp
                                  1               5 ccc gcc cat tga acc aaa tgg gaa aag aag cga agc ctc tct ctt gga     1182
Pro Ala His     Thr Lys Trp Glu Lys Lys Arg Ser Leu Ser Leu Gly
 10              15                  20 cat atg c gaggtttact cttctctttg ctgatctagt tgcatttgtt tagttgaaga    1239
His Met
 25 taccatttga gttctctcgg aaattttgag gactagctct aatccctgta gttgatttct   1299 tattgcag aa agt tct gtc tct tga tgg gag cac ttg cga tga agc ttt     1348
         Gln Ser Ser Val Ser     Trp Glu His Leu Arg     Ser Phe
                    30                       35 gaa gtt gtt tac aga aac caa acg aat ttt gtc agc aag cat gtc taa    1396
Glu Val Val Tyr Arg Asn Gln Thr Asn Phe Val Ser Lys His Val
 40                  45                  50 cat tgg aag tgg aa cggtgaaata cattttcct ctaacttctc ttttatcagt     1450
His Trp Lys Trp Lys
    55
```

```
taactgtggt tcattatga ctaaatcctt ttttcttctt cttatta g cgg gaa gaa      1507
                                                   Arg Glu Glu
                                                        60 gta gag agg ttc tgg ttt gcg ttt att ctc tat tca gtg aag agg ctt      1555
Val Glu Arg Phe Trp Phe Ala Phe Ile Leu Tyr Ser Val Lys Arg Leu
         65                  70                  75 agt gtg aga aaa gaa gcg gat ggt ctg tca gtg tct ggt gat aat gag      1603
Ser Val Arg Lys Glu Ala Asp Gly Leu Ser Val Ser Gly Asp Asn Glu
     80                  85                  90 ttt aat cta tgt cag ata ctg agg gct ctg aag cta aa  gtaagtagtg      1651
Phe Asn Leu Cys Gln Ile Leu Arg Ala Leu Lys Leu Lys
 95                 100                 105 ttcaattctt ccttccttgt cattcttaaa ttcatttgta gtgacgattt tcctcttttc    1711
tgtttatagt a ttg tgg att ttt tta aag agt tac ctc agt ttg tgg tca     1761
             Leu Trp Ile Phe Leu Lys Ser Tyr Leu Ser Leu Trp Ser
                         110                 115 agg ctg gat ctg tac tgg gtg aac ttt acg gcg cag act ggg aga aca      1809
Arg Leu Asp Leu Tyr Trp Val Asn Phe Thr Ala Gln Thr Gly Arg Thr
120             125                 130                 135 gac ttc ag  gttttgacta acatctttta aatatacttc tacttctatt             1857
Asp Phe Arg atatcattgt taaatatgct tctattaact aattttact tacta g gca aag gag       1912
                                                Ala Lys Glu
                                                    140 gtg cag gct aac ttt gtg cat ctt agc ctt cta agc aag tgagtttagc       1961
Val Gln Ala Asn Phe Val His Leu Ser Leu Leu Ser Lys
            145                 150 tcccttccta ttttacattt atctttgttt tgtgtaagaa tagttattga catagatttc    2021
atattttgga cctgcaactt agaagcaaat tttcttccta tgcaataatc agaatatggg    2081
cttgcaatat tccttccatt ttaaattaat taagatttag agttacagat ttctggtttt    2141
catgtgatta tattctgtga attgttttaa ggacatgtta aagtatgatg ttttttggtac   2201 ctttccttgg taaca gat act aca aac gtg ggt tcc ggg aat tct ttt tga     2252
                 Asp Thr Thr Asn Val Gly Ser Gly Asn Ser Phe
                     155                 160                 165 cat atg atg caa acg cag aaa aga act cag caa act ctt cta cct att      2300
His Met Met Gln Thr Gln Lys Arg Thr Gln Gln Thr Leu Leu Pro Ile
            170                 175                 180 tgc tgg ata gtt atc gtt ttg gat ggc tac tct ttt tgg cac tcc gaa      2348
Cys Trp Ile Val Ile Val Leu Asp Gly Tyr Ser Phe Trp His Ser Glu
            185                 190                 195 acc atg cgt tta gtc gat tta agg acc tcg tga cat gct caa atg gcg      2396
Thr Met Arg Leu Val Asp Leu Arg Thr Ser     His Ala Gln Met Ala
        200                 205                         210 tag ttt cta tat t ggttagtgac tacctgtgga gctctcccta atctttcatt        2449
    Phe Leu Tyr
        215 cattttagtc ttgctgtaca ttattacttg aaagatgctt cgtttaatat aacgcaattg    2509
aagtataggc taactccttt tcatgttatc a gg  cta ttt tga tca tac atg      2560
                                      Trp Leu Phe     Ser Tyr Met
                                                              220 ttc ctt gtc ggt tta gaa att tca gca tcc aag att ctt ctc gct t        2606
Phe Leu Val Gly Leu Glu Ile Ser Ala Ser Lys Ile Leu Leu Ala
            225                 230                 235 tggtgagtgt ttatctttc ttctatcccg ataaccatgg caccatagaa tgtttatcat     2666
ctattttcat ttatgtgatg aatctca gt  taa gaa agg tga caa agg tgt aga    2719
                        Cys     Glu Arg     Gln Arg Cys Arg
                                        240
```

-continued

```
ctt ggt tgc atc act ttg caa gat ata tga cgc ctc aga aga tga gtt      2767
Leu Gly Cys Ile Thr Leu Gln Asp Ile     Arg Leu Arg Arg     Val
    245                 250                     255 gag gat agt aat tga caa ggc aaa taa ttt ggt aga aac cat act gaa      2815
Glu Asp Ser Asn     Gln Gly Lys     Phe Gly Arg Asn His Thr Glu
            260                 265                     270 gaa aaa gcc atc tcc agc atc tga gtg cca aac tga caa gct aga taa      2863
Glu Lys Ala Ile Ser Ser Ile     Val Pro Asn     Gln Ala Arg
                275                 280 tat tga ccc a ggttggtcta aaatcatttt ccttcttcaa ttaaagaatc            2913
Tyr     Pro
285 atgtgagttc attgaacagt tgcctgattg ttcttcgaat ctatatggtg ttttactgca    2973 ga  tgg ctt gac cta ctt tga gga ttt act gga aga gac gtc cat ctc      3020
Arg Trp Leu Asp Leu Leu     Gly Phe Thr Gly Arg Asp Val His Leu
            290         295                         300 aac tag ctt aat tac act tga aaa gga tta cta tga tgg taa agg cga      3068
Asn     Leu Asn Tyr Thr     Lys Gly Leu Leu     Trp     Arg Arg
                305                 310 act tga tga gag ggt att cat caa tga aga gga tag ctt act tgg atc      3116
Thr         Glu Gly Ile His Gln     Arg Gly     Leu Thr Trp Ile
                315                     320                 325 tgg aag ctt atc tgc agg agc tgt taa tat tac tgg tgt taa gag gaa      3164
Trp Lys Leu Ile Cys Arg Ser Cys     Tyr Tyr Trp Cys     Glu Glu
                330                     335 aat tga tgc ttt gag ctc acc tgc aag gac att tat aag ccc act ttc      3212
Asn     Cys Phe Glu Leu Thr Cys Lys Asp Ile Tyr Lys Pro Thr Phe
340                         345                 350 tcc tca taa gtc gcc tgc tgc taa gac aaa tgg tat tag cgg tgc tac      3260
Ser Ser     Val Ala Cys Cys     Asp Lys Trp Tyr     Arg Cys Tyr
355                 360                         365 caa gtt ggc agc aac acc agt gag cac agc aat gac aac tgc caa gtg      3308
Gln Val Gly Ser Asn Thr Ser Glu His Ser Asn Asp Asn Cys Gln Val
            370                 375                 380 gct cag gac tgt cat atc ccc gct tct gcc aaa acc ttc tcc tgg gtt      3356
Ala Gln Asp Cys His Ile Pro Ala Ser Ala Lys Thr Phe Ser Trp Val
    385                 390                 395 gga aca ttt cct taa atc atg tga tag gga tat aac aaa tga cgt cac      3404
Gly Thr Phe Pro     Ile Met     Gly Tyr Asn Lys     Arg His
400                     405                         410 acg aag agc aca cat aat att gga agc tat ttt ccc aaa tag ttc cct      3452
Thr Lys Ser Thr His Asn Ile Gly Ser Tyr Phe Pro Lys     Phe Pro
                415                 420                 425 tgg tgc cca atg tgg agg tgg aag ttt gca agc tgt tga cct gat gga      3500
Trp Cys Pro Met Trp Arg Trp Lys Phe Ala Ser Cys     Pro Asp Gly
            430                 435                     440 tga cat atg ggc aga gca gcg cag att aga agc ttg taa gtt ata cta      3548
    His Met Gly Arg Ala Ala Gln Ile Arg Ser Leu     Val Ile Leu
                445                 450                     455 cag agt tct tga ggc aat gtg taa agc aga agc tca gat ttt gca tgc      3596
Gln Ser Ser     Gly Asn Val     Ser Arg Ser Ser Asp Phe Ala Cys
                    460                 465 aaa taa tct gaa ctc ttt att gac aaa tga gag gtt cca tag atg cat      3644
Lys     Ser Glu Leu Phe Ile Asp Lys     Glu Val Pro     Met His
470                 475                 480 gct tgc ttg ctc agc tga att ggt act ggc tac cca caa aac aat tac      3692
Ala Cys Leu Leu Ser     Ile Gly Thr Gly Tyr Pro Gln Asn Asn Tyr
            485                 490                 495
```

-continued

```
aat gtt gtt ccc agc tgt tct gga gag gac tgg gat cac agc ctt tga      3740
Asn Val Val Pro Ser Cys Ser Gly Glu Asp Trp Asp His Ser Leu
        500                 505                 510 tct cag caa ggt aat tga gag ttt cat acg aca tga aga ttc tct gcc      3788
Ser Gln Gln Gly Asn     Glu Phe His Thr Thr     Arg Phe Ser Ala
        515                 520                 525 tag aga gtt gag acg aca tct gaa ttc act gga gga acg gct tct aga      3836
    Arg Val Glu Thr Thr Ser Glu Phe Thr Gly Gly Thr Ala Ser Arg
            530                 535                 540 gag tat ggt atg gga gaa agg ctc ttc aat gta caa ttc tct gat tgt      3884
Glu Tyr Gly Met Gly Glu Arg Leu Phe Asn Val Gln Phe Ser Asp Cys
        545                 550                 555 tgc cag gcc atc gct tgc att gga gat aaa tca gct cgg ttt act agc      3932
Cys Gln Ala Ile Ala Cys Ile Gly Asp Lys Ser Ala Arg Phe Thr Ser
        560                 565                 570 tga acc aat gcc atc tct gga tgc aat cgc agc act tat taa ttt ctc      3980
    Thr Asn Ala Ile Ser Gly Cys Asn Arg Ser Thr Tyr     Phe Leu
        575                 580                 585 tga cgg agc aaa tca tgc atc atc tgt aca aaa gca tga aac ttg tcc a    4029
    Arg Ser Lys Ser Cys Ile Ile Cys Thr Lys Ala     Asn Leu Ser
        590                 595                 600 ggtagtttta tttgtttctg aattaaagca gttttccaac ctgctgttaa tggtatgatt    4089
ttcttaccaa aaattgtcaa atttgctgcc atata gg  aca aaa tgg ggg gat       4141
                                       Arg Thr Lys Trp Gly Asp
                                                       605 tag atc gcc caa aag att atg tac tga tta ccg cag cat tct agt tga      4189
    Ile Ala Gln Lys Ile Met Tyr     Leu Pro Gln His Ser Ser
        610                 615                 620 acg caa ttc ctt tac atc acc agt aaa gga tcg tct gtt ggc ctt agg      4237
Thr Gln Phe Leu Tyr Ile Thr Ser Lys Gly Ser Ser Val Gly Leu Arg
        625                 630                 635 caa cgt taa atc caa gat gct gcc acc tcc gtt gca gtc tgc att tgc      4285
Gln Arg     Ile Gln Asp Ala Ala Thr Ser Val Ala Val Cys Ile Cys
            640                 645                 650 ca  ggtacatttt gagtaactat gagtagaaat ggagagttag tttacctatc           4337
Gln tagttgtccc tgtacttgtt aagtaacctc ttcggattta tgtctaca g ccc aac       4392
                                                       Pro Asn acg gcc caa ccc agg agg tgg agg aga aac ttg tgc aga aac tgg aat      4440
Thr Ala Gln Pro Arg Arg Trp Arg Arg Asn Leu Cys Arg Asn Trp Asn
655                 660                 665                 670 caa tat ttt ctt cac aaa ggtaggtctg tgagatcttt ggatctacta             4488
Gln Tyr Phe Leu His Lys
                675 ctaatcgttt ggttagatga tgtactacaa aacacggtat tgattcttca ttttcggctg    4548 ggaattgtgt taaatgtggt ggctcttccc a gat taa taa att ggc tgc tgt       4600
                                  Asp         Ile Gly Cys Cys
                                                        680 aag aat caa tgg aat ggt gga aag act aca act ttc aca gca aat aag      4648
Lys Asn Gln Trp Asn Gly Gly Lys Thr Thr Thr Phe Thr Ala Asn Lys
        685                 690                 695 gga gag tgt gta ttg ttt ctt cca aca tgt act tgc tca gcg gac ttc      4696
Gly Glu Cys Val Leu Phe Leu Pro Thr Cys Thr Cys Ser Ala Asp Phe
        700                 705                 710 tct ttt att cag tcg aca cat tga cca gat cat tct ctg ttg ctt cta     4744
Ser Phe Ile Gln Ser Thr His     Pro Asp His Ser Leu Leu Leu Leu
        715                 720                 725 cgg agt ggc caa ggtgagtagt gtgattcaaa gggtttaact atatgtcatc         4796
```

```
                                                                        -continued Arg Ser Gly Gln
    730 tggtttacaa tggcttctct tacacttaca ctttttccat gaatcacctt gtagatatcc       4856 caaatgagcc tga ctt tca ggg aaa tca tat aca act acc gga agc aac         4905
            Leu Ser Gly Lys Ser Tyr Thr Thr Thr Gly Ser Asn
                735                 740 cac agt gta aac cat tag ttt tcc gca gcg ttt atg tgg atg cgt tac         4953
His Ser Val Asn His     Phe Ser Ala Ala Phe Met Trp Met Arg Tyr
745             750                 755 aat gtc gcc gtc aag g ggtatatata cactcttaac cttatgctga aaagtttctt      5009
Asn Val Ala Val Lys
760 tactcggtgg agaagactaa atttgtgaca atgacttgaa ca ga  gaa tag ggc         5062
                                               Gly Glu     Gly cag atc atg ttg aca tca tca cat tct aca atg aaa tat tta ttc ctg         5110
Gln Ile Met Leu Thr Ser Ser His Ser Thr Met Lys Tyr Leu Phe Leu
            770                 775                 780 ccg taa agc cgc tgc tgg tgg agc tag gtc ctg taa gaa acg acc ggg         5158
Pro     Ser Arg Cys Trp Trp Ser     Val Leu     Glu Thr Thr Gly
            785                 790                     795 ctg tgg aag cca ata ata agc ctg aa  ggtagttaag aaaggccaga               5204
Leu Trp Lys Pro Ile Ile Ser Leu Lys
                800 tacttgttag atgtaagctt tgtctatcaa tttagtccct aagttaaatg atcgtcttat       5264 tttggattca ca g gtc aat gtc ccg gat cgc caa agg tgt ctg tgt ttc        5313
              Val Asn Val Pro Asp Arg Gln Arg Cys Leu Cys Phe
                            810                 815 caa gtg ttc cag aca tgt ccc cta aaa aag tat ctg cag tgc aca atg         5361
Gln Val Phe Gln Thr Cys Pro Leu Lys Lys Tyr Leu Gln Cys Thr Met
            820                 825                 830 ttt atg ttt ctc ctc ttc ggg gat caa ag  gtaaagaaga tcatagtgct           5410
Phe Met Phe Leu Leu Phe Gly Asp Gln Arg
            835                 840 taactctttta tcatgatatg actaagtctt gaggaggagg taggtgacaa gattgtttgg      5470
ttaccttcca tgtgttgtgt gtttgca g atg gat gct ctt att tca cac agt        5522
                                Met Asp Ala Leu Ile Ser His Ser
                                845                 850 aca aag agt tac tat gct tgt gtt gga gag agt aca cat gct tac cag         5570
Thr Lys Ser Tyr Tyr Ala Cys Val Gly Glu Ser Thr His Ala Tyr Gln
            855                 860                 865 agc cct tca aag gac cta tct gcc atc aac aac cgc ttg aac a               5613
Ser Pro Ser Lys Asp Leu Ser Ala Ile Asn Asn Arg Leu Asn
            870                 875                 880 agtaagtaaa aaaatcacgt ctctcatcag cttcttccat aaaaccaatc actgacccaa       5673
tccaatttca tctggtgtca ca gc  agc agc agc aac cgc aag agg acg cta       5724
                             Ser Ser Ser Ser Asn Arg Lys Arg Thr Leu
                                            885                 890 aac ttt gac gca gaa gca ggg atg gtc agc gat tcc atg gta gca aat         5772
Asn Phe Asp Ala Glu Ala Gly Met Val Ser Asp Ser Met Val Ala Asn
            895                 900                 905 agc ctt aac ctc caa aac caa aat caa aac caa aat gga agc gat gca         5820
Ser Leu Asn Leu Gln Asn Gln Asn Gln Asn Gln Asn Gly Ser Asp Ala
            910                 915                 920 tcg tcc tca ggt ggt gcc gca ccc ctt aaa acc gag cca aca gat tca         5868
Ser Ser Ser Gly Gly Ala Ala Pro Leu Lys Thr Glu Pro Thr Asp Ser
            925                 930                 935 ta gatatctctc tctacttgct acaccaactt ctcttcagtt atagcatctg               5920
```

```
taaatcctta tgttgcagag tttgctttta tgtttagctt tctagtttat agtgatcacc    5980
tcaggctatg agcggatgga tccctttatt gtttctttt  tctttttta  tcttagttaa    6040 gtcagtctta ataagcatta ataaatgtct ttttcttgtt cactctttct aactgtgttc    6100
ggtgtcccat ctactaaatt tattttccac tttaaaaaaa aacaatttgt gacatttact    6160
taacttggaa catatacagt acagttaagc aattaactat aaccaacaaa ttgtctgaac    6220
aattgtctgt cttacctttt tagctctcta taaatttacg ccgcaaaaca cactttatg     6280 tcgatttcag aataacttac tactccagca tatttctcaa aactttctca ataggttaaa    6340
tttaaaacaa ccttgcaact tatgaaaaaa tcctccagca aatttgccag aaaagaatgt    6400
tacaatggct acaatcacat cc                                             6422
```